US008337701B2

(12) United States Patent
Martin et al.

(10) Patent No.: US 8,337,701 B2
(45) Date of Patent: Dec. 25, 2012

(54) INTRAVENOUS FILTER

(75) Inventors: Charles J. Martin, Dexter, MI (US);
Jeffrey J. Toma, Ann Arbor, MI (US)

(73) Assignee: Pall Corporation, Port Washington, NY (US)

( * ) Notice: Subject to any disclaimer, the term of this patent is extended or adjusted under 35 U.S.C. 154(b) by 36 days.

(21) Appl. No.: 13/047,124

(22) Filed: Mar. 14, 2011

(65) Prior Publication Data

US 2012/0234757 A1 Sep. 20, 2012

(51) Int. Cl.
*B01D 29/50* (2006.01)
*B01D 35/00* (2006.01)
*B01D 37/00* (2006.01)
*B01D 61/00* (2006.01)

(52) U.S. Cl. ........ 210/649; 210/420; 210/428; 210/435; 210/436; 210/472; 210/650; 210/767; 96/6

(58) Field of Classification Search .................. 210/645, 210/649, 650, 767, 188, 232, 321.6, 420, 210/428, 435, 436, 455, 472, 484, 340, 341; 96/6
See application file for complete search history.

(56) References Cited

U.S. PATENT DOCUMENTS

| 4,925,572 | A | 5/1990 | Pall |
| 5,439,587 | A | 8/1995 | Stankowski et al. |
| 5,622,626 | A | 4/1997 | Matkovich et al. |
| 5,827,429 | A | 10/1998 | Ruschke et al. |
| 6,231,770 | B1 | 5/2001 | Bormann et al. |
| 6,328,789 | B1 | 12/2001 | Spranger |
| 6,347,711 | B1 | 2/2002 | Goebel et al. |
| 2004/0226444 | A1 | 11/2004 | Leahey |
| 2005/0133439 | A1 | 6/2005 | Blickhan |

FOREIGN PATENT DOCUMENTS

| CN | 2699913 Y | 5/2005 |
| CN | 201399117 Y | 2/2010 |
| DE | 197 50 062 A1 | 5/1999 |
| DE | 199 28 476 A1 | 12/1999 |
| EP | 0 333 119 A2 | 9/1989 |
| EP | 0 552 090 A1 | 7/1993 |
| EP | 1 208 857 A1 | 5/2002 |
| EP | 1 421 960 A1 | 5/2004 |
| EP | 1 442 761 A2 | 8/2004 |
| EP | 2 255 861 A1 | 12/2010 |
| GB | 2 094 655 A | 9/1982 |
| WO | 95/03842 A1 | 2/1995 |

OTHER PUBLICATIONS

European Search Report, Application No. EP 12 15 8283.7, mailed Jul. 7, 2012.
Search Report, Singapore Application No. 201201597-0, mailed Aug. 10, 2012.
Search Report, Australian Application No. 2012201468, mailed Sep. 7, 2012.

*Primary Examiner* — John Kim
(74) *Attorney, Agent, or Firm* — Leydig, Voit & Mayer, Ltd.

(57) ABSTRACT

Intravenous fluid filter devices including a filter comprising spaced apart first and second filter elements comprising hydrophilic membranes and providing inside-out flow, and methods of using the devices, are disclosed.

10 Claims, 13 Drawing Sheets

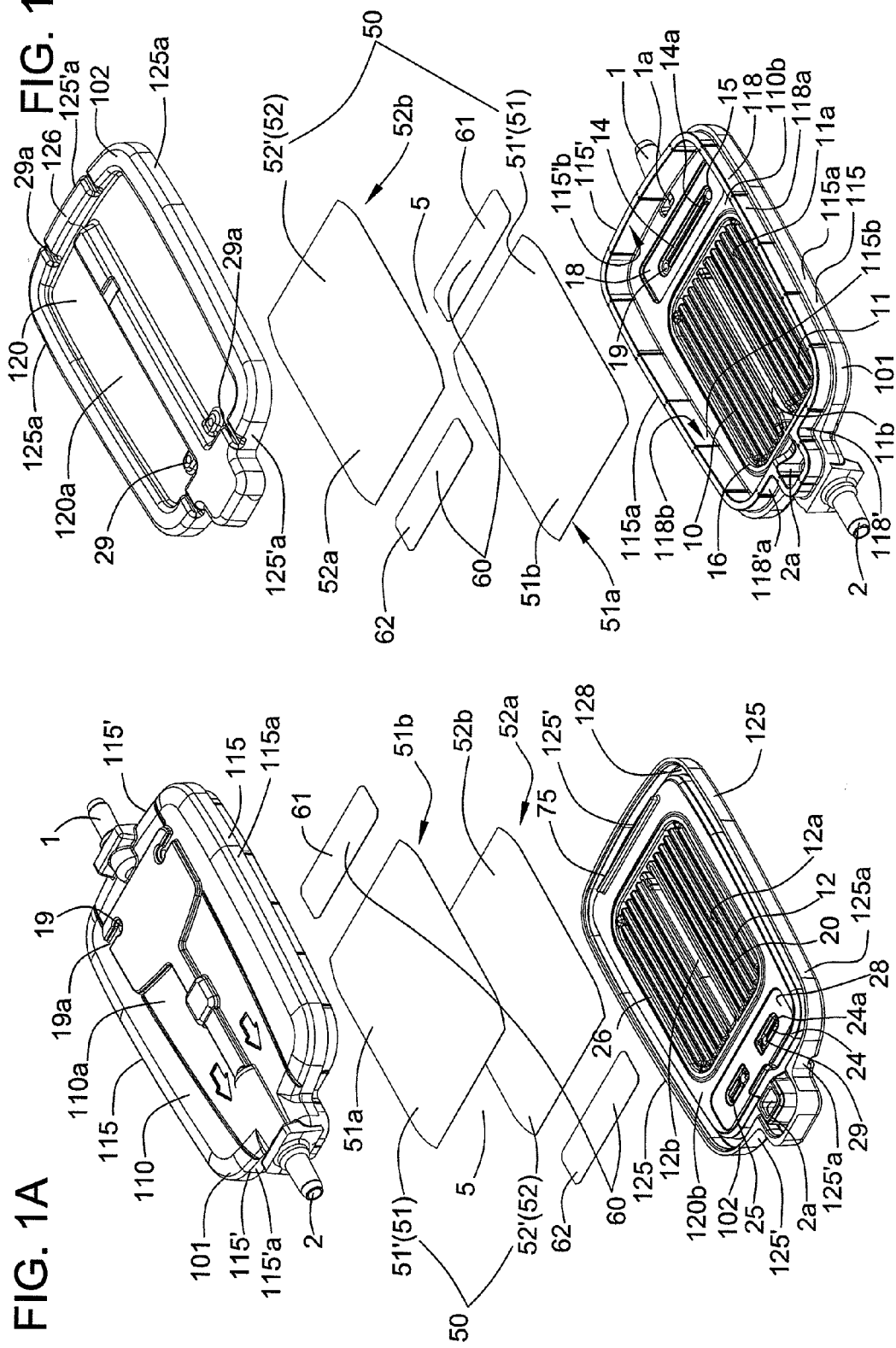

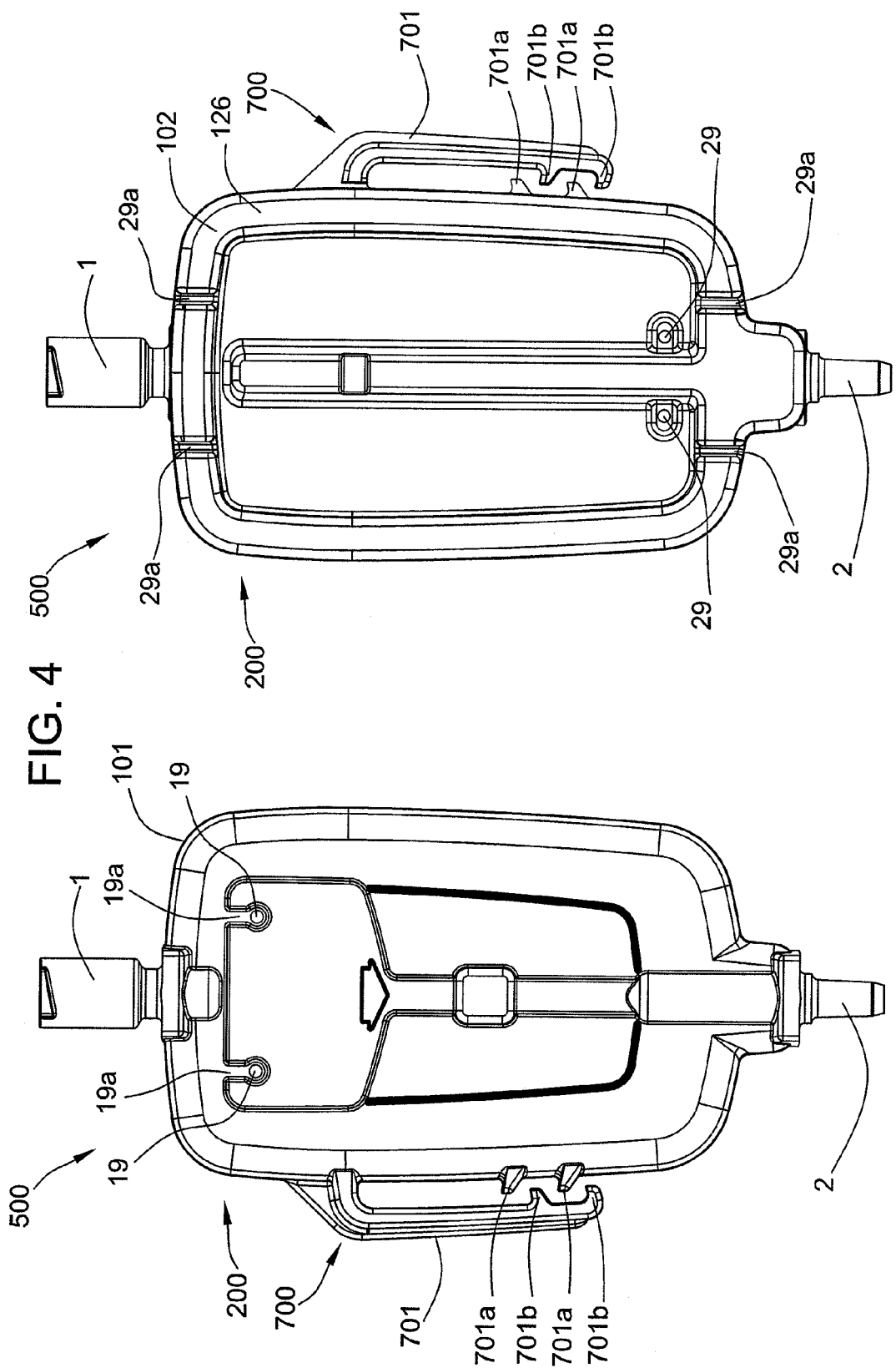

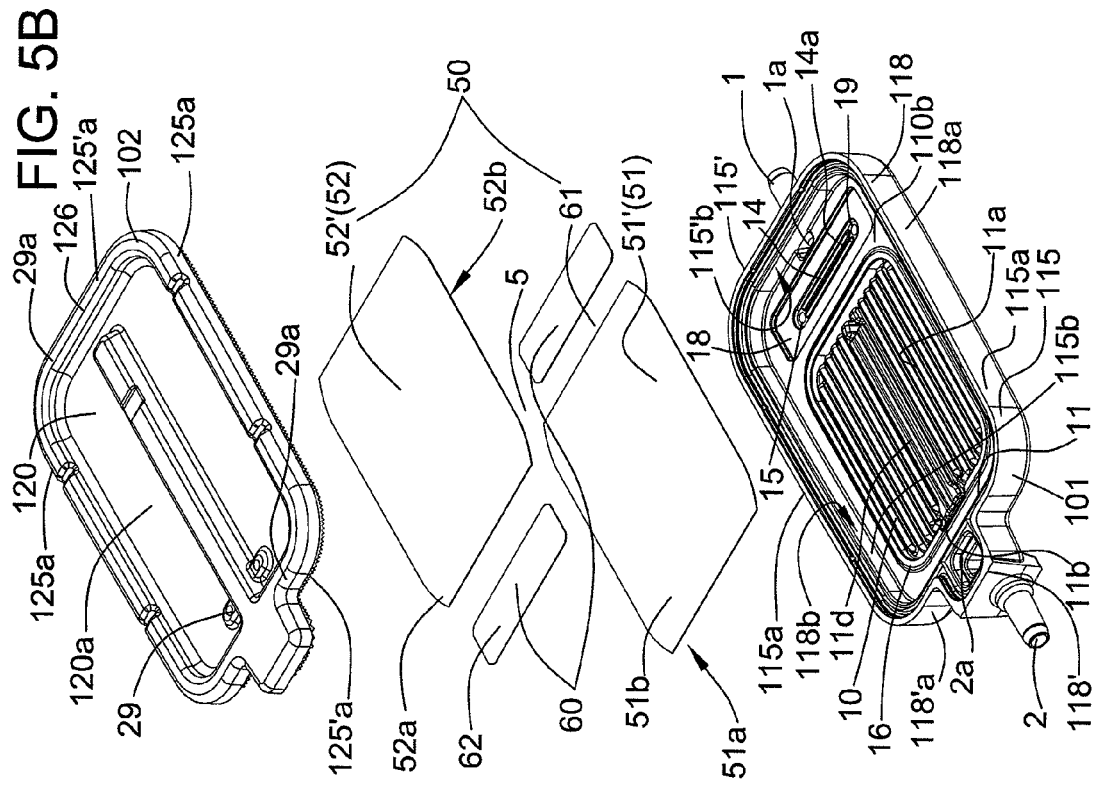

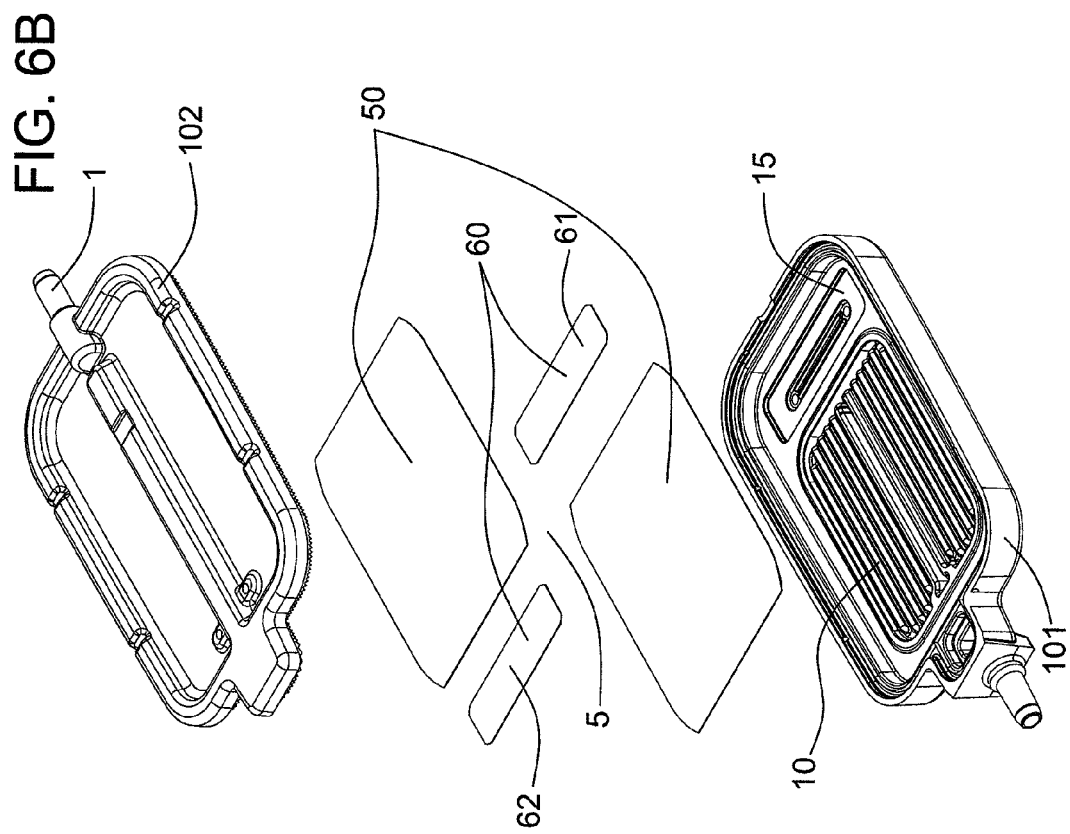
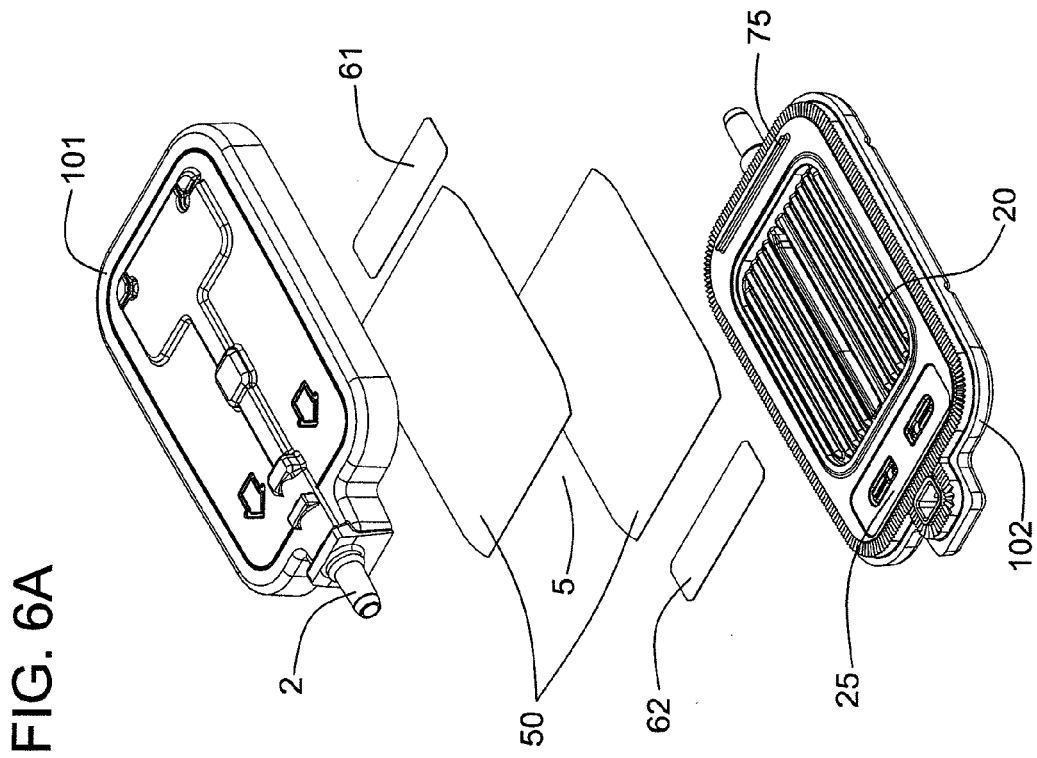

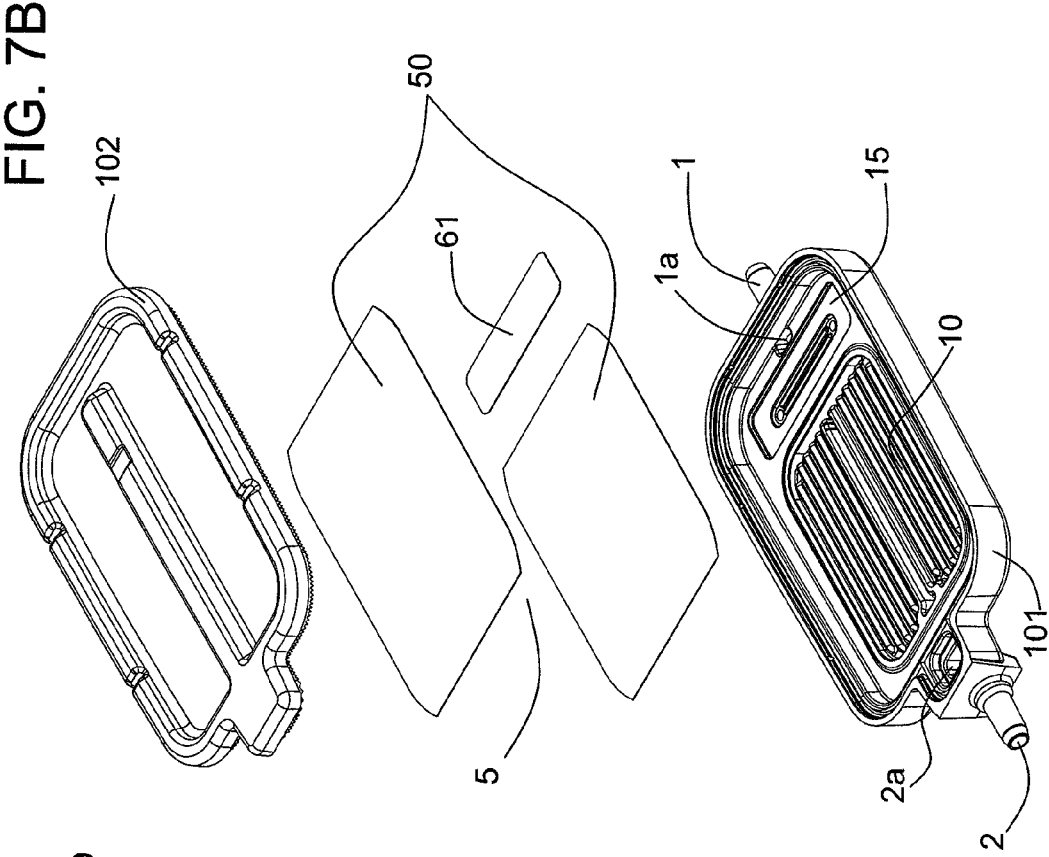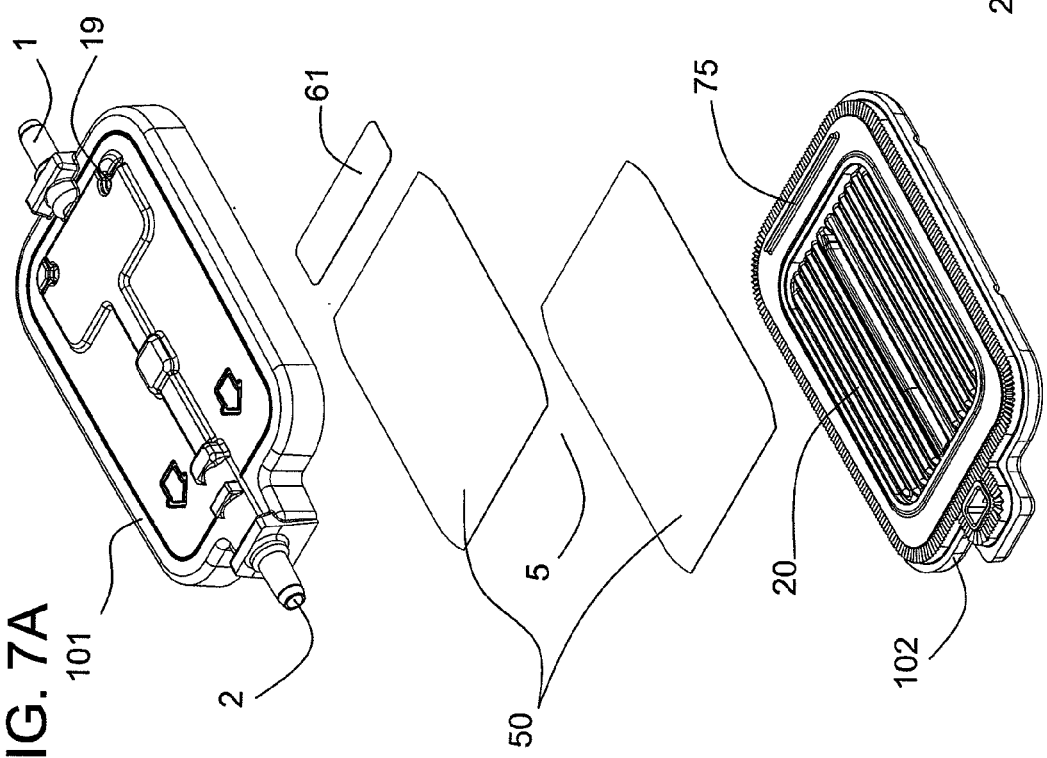

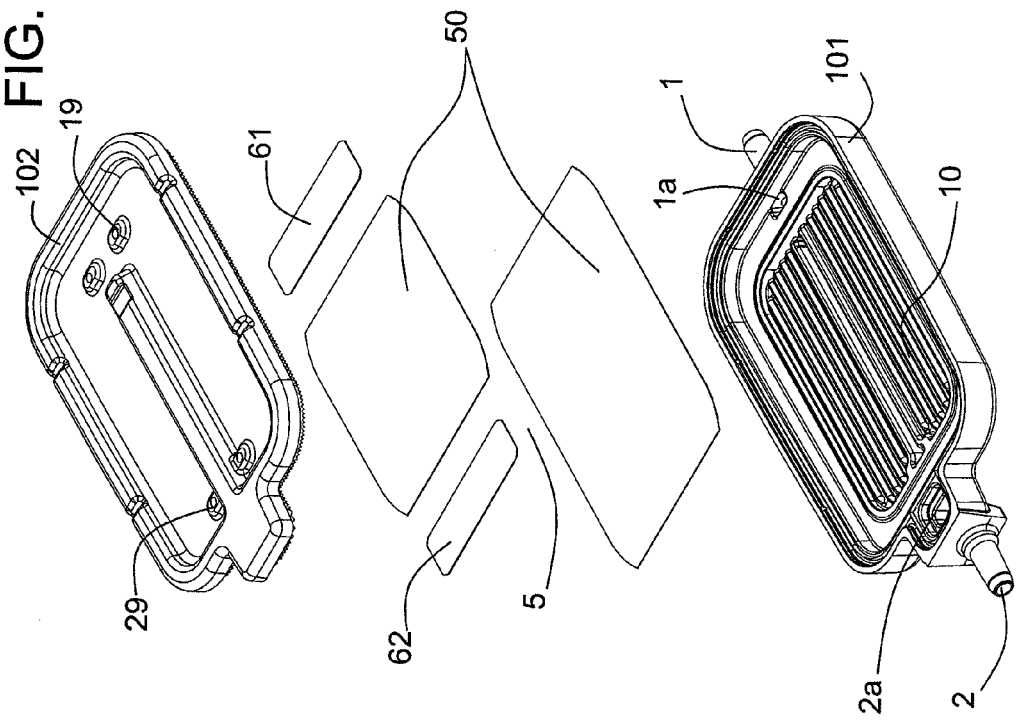
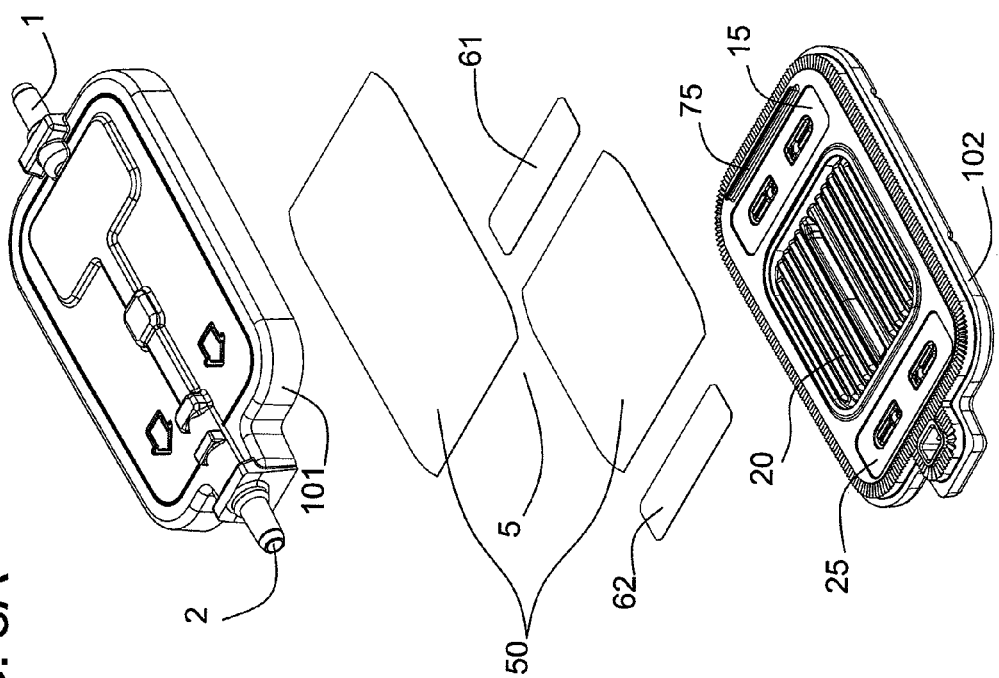

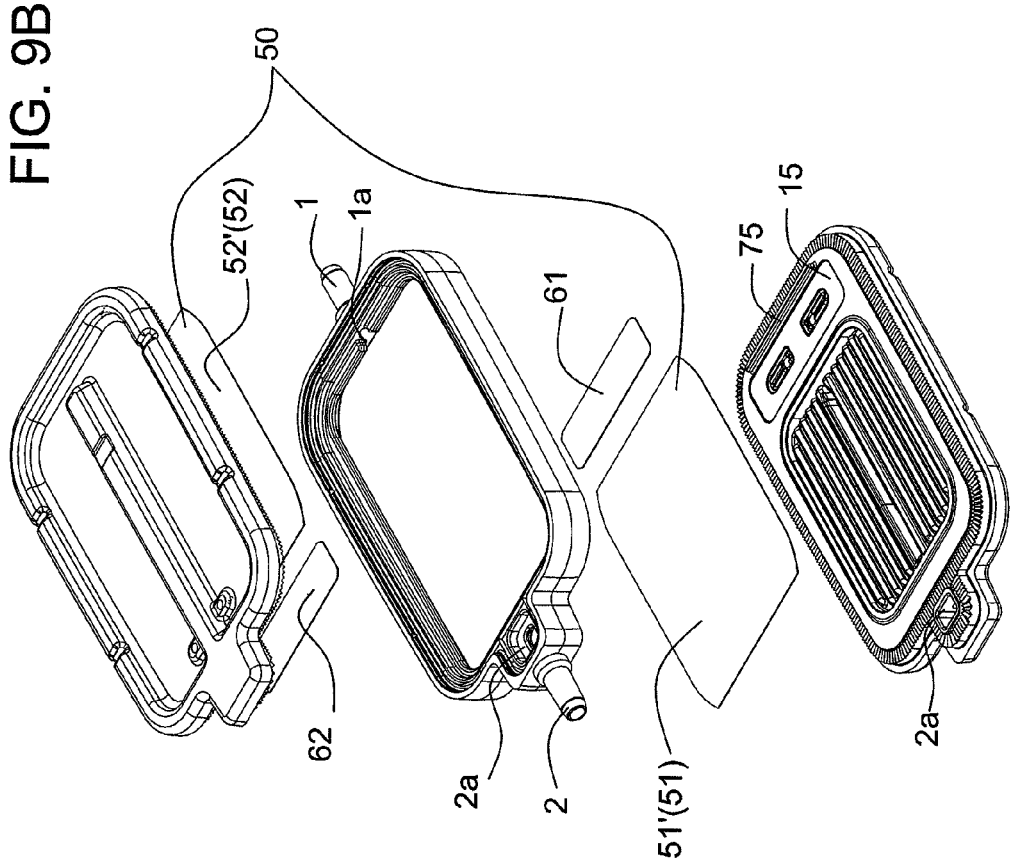
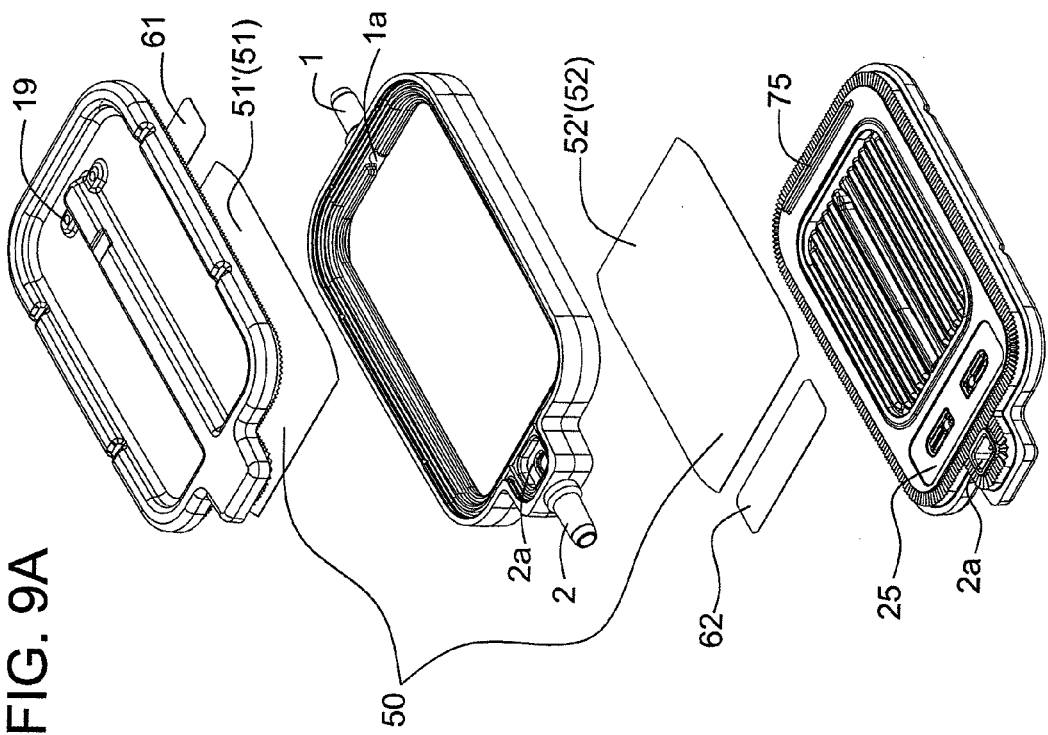

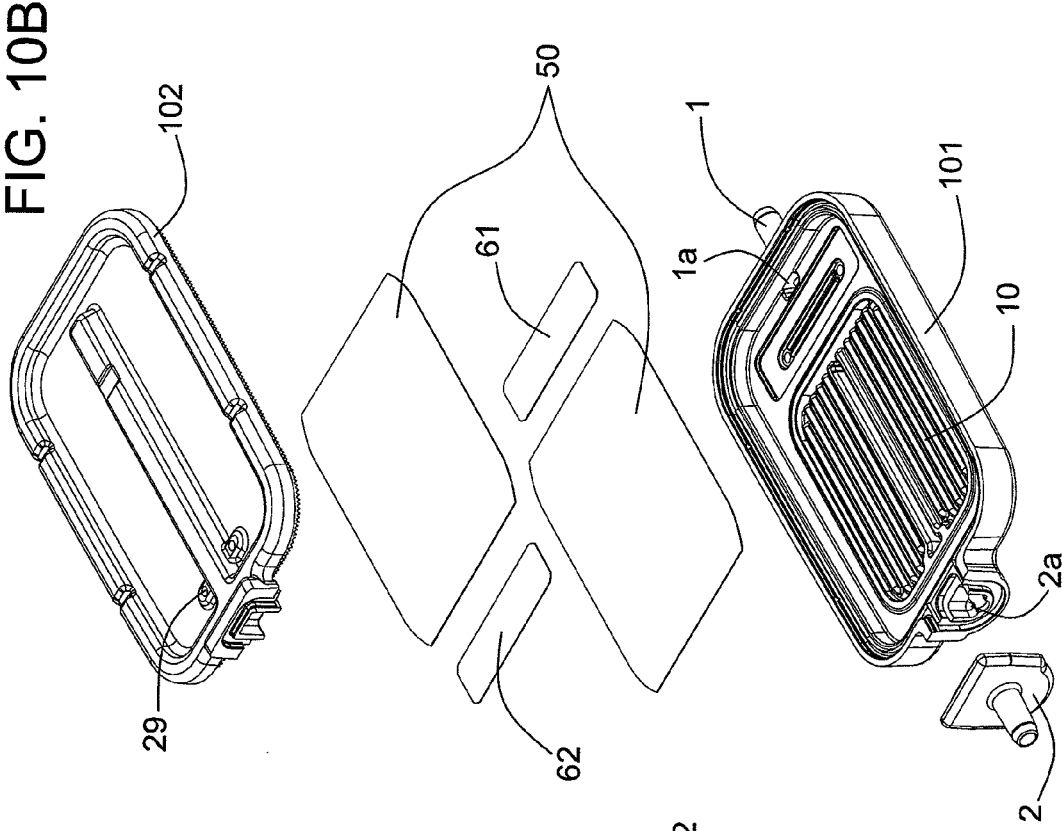
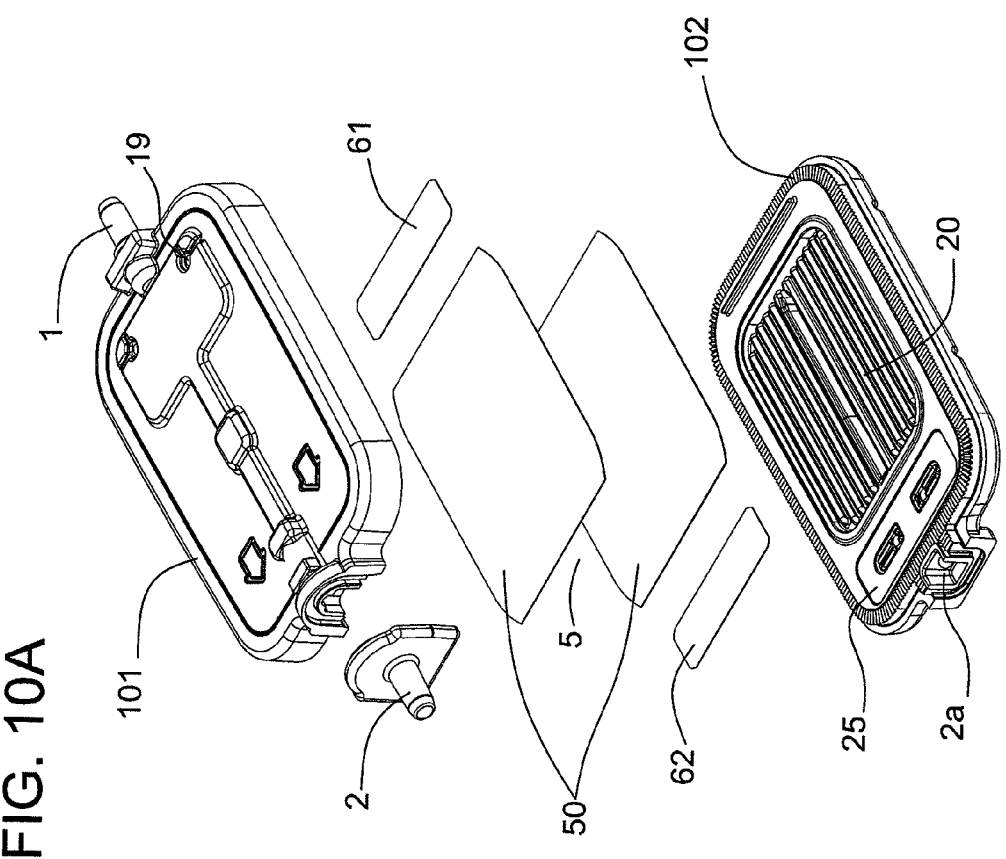

INTRAVENOUS FILTER

BACKGROUND OF THE INVENTION

Intravenous (IV) fluids are typically filtered to remove undesirable material(s) from the fluid before supplying the fluid to a patient. In order to prevent air from entering the vein of a patient, in-line IV filter devices preferably provide for liquid-air (gas) separation. Additionally, air in the tubing and device housing downstream of the filter element must be removed before IV fluid is supplied to the patient, and efficiently removing remaining air, e.g., small gas bubbles, can involve manipulation, such as tapping on the device housing to dislodge the bubbles.

In order to reduce the size of IV filter devices, some devices have been provided having two separate filter elements utilized for "outside-in" flow, wherein two fluid flow paths are provided along first and second outside inlet portions to a common central outlet portion. A portion of fluid to be filtered passes along a first fluid flow path from a device inlet and a first outside inlet portion of the housing, through a first filter element, and into a common outlet portion, and another portion of fluid to be filtered passes along a second fluid flow path from the device inlet and a second outside inlet portion of the housing, through a second filter element, and into the common outlet portion. The filtered fluid passes from the common outlet portion and through the device outlet and through tubing to the patient.

However, there is a need for improved IV filter devices and methods of supplying IV fluids to patients.

BRIEF SUMMARY OF THE INVENTION

An embodiment of the invention provides a filter device comprising a housing comprising at least a first section and a second section, (i) the first section comprising a top wall comprising an outer surface and an inner surface, the first section including a first filtrate downstream chamber, the first filtrate downstream chamber including a portion of the inner surface of the top wall, (ii) the second section comprising a bottom wall comprising an outer surface and an inner surface, the second section including a second filtrate downstream chamber, the second filtrate downstream chamber including a portion of the inner surface of the bottom wall; wherein the first section including the first filtrate downstream chamber also includes at least one first vent chamber, and the first vent chamber includes another portion of the inner surface of the top wall and/or wherein the second section including the second filtrate downstream chamber also includes at least one second vent chamber, and the second vent chamber includes another portion of the inner surface of the bottom wall; the housing further comprising an inlet, an outlet, at least one side wall having a side wall inner surface, and a cavity bordered by the inner surfaces of the top and bottom walls, and the inner surface of the at least one side wall; a filter comprising at least first and second spaced apart porous filter elements, each filter element comprising a hydrophilic membrane, the first and second filter elements each having an upstream surface and a downstream surface, the first filter element being disposed in the housing across a first fluid flow path, and the second filter element being disposed in the housing across a second fluid flow path; the housing including, in the cavity, an upstream inlet chamber between the upstream surfaces of the first and second filter elements and bordered by the inner surface of the at least one side wall and the upstream surfaces of the filter elements; the housing defining the first fluid flow path between the inlet, the upstream inlet chamber, the first filtrate downstream chamber and the outlet, wherein the first filter element is disposed across the first fluid flow path; and, defining the second fluid flow path between the inlet, the upstream inlet chamber, the second filtrate downstream chamber and the outlet, wherein the second filter element is disposed across the second fluid flow path.

In a preferred embodiment of the device, the upstream inlet chamber is free of a solid partition between the upstream surfaces of the first and second filter elements.

In an embodiment, the device further comprises central channels in the first and/or second filtrate downstream chambers that are covered for the majority of the length of the channels.

Yet another embodiment comprises a filter device comprising a housing comprising a first section and a second section, (i) the first section comprising a top wall comprising an outer surface and an inner surface, and at least one side wall, the first section including a first filtrate downstream chamber, the first filtrate downstream chamber including a portion of the inner surface of the top wall, (ii) the second section comprising a bottom wall comprising an outer surface and an inner surface, and at least one side wall, the second section including a second filtrate downstream chamber, the second filtrate downstream chamber including a portion of the inner surface of the bottom wall; the housing further comprising an inlet and an outlet, and a cavity bordered by the inner surfaces of the top and bottom walls, and an inner surface of at least one side wall of the first and/or second section; a filter comprising at least first and second spaced apart porous filter elements, each filter element comprising a hydrophilic membrane, the first and second filter elements each having an upstream surface and a downstream surface, the first filter element being disposed in the housing across a first fluid flow path, and the second filter element being disposed in the housing across a second fluid flow path; the housing including, in the cavity, an upstream inlet chamber between the upstream surfaces of the first and second filter elements and bordered by the inner surface of at least one side wall of the first and/or second section and the upstream surfaces of the filter elements; the housing defining the first fluid flow path between the inlet, the upstream inlet chamber, the first filtrate downstream chamber and the outlet, wherein the first filter element is disposed across the first fluid flow path; and, defining the second fluid flow path between the inlet, the upstream inlet chamber, the second filtrate downstream chamber and the outlet, wherein the second filter element is disposed across the second fluid flow path; wherein the top wall inner surface of the first filtrate downstream chamber and the bottom wall inner surface of the second filtrate downstream chamber each comprise a plurality of ridges providing a plurality of channels, the channels directing fluid from the downstream surfaces of the first and second filter elements to the housing outlet and wherein the top wall inner surface of the first filtrate downstream chamber and the bottom wall inner surface of the second filtrate downstream chamber each comprise a central channel that is wider and/or deeper than the other channels, and, wherein each central channel has side, top, and bottom walls forming a closed tube for at least a majority of the length of each central channel.

In another embodiment, a filter device is provided comprising a housing comprising a first section and a second section, (i) the first section comprising a top wall comprising an outer surface and an inner surface, and at least one side wall, the first section including a first filtrate downstream chamber and a first vent chamber, the first filtrate downstream chamber including a portion of the inner surface of the top wall, and the first vent chamber including another portion of the inner surface of the top wall, (ii) the second section comprising a bottom wall comprising an outer surface and an inner surface, and at least one side wall, the second section including a second filtrate downstream chamber and a second vent chamber, the second filtrate downstream chamber including a portion of the inner surface of the bottom wall, and the second vent chamber including another portion of the inner surface of the bottom wall; the housing further comprising an inlet and an outlet, and a cavity bordered by the inner surfaces of the top and bottom walls, and an inner surface of at least one side wall of the first and/or second section; a filter comprising at least first and second spaced apart porous filter elements, each filter element comprising a hydrophilic membrane, the first and second filter elements each having an upstream surface and a downstream surface, the first filter element being disposed in the housing across a first fluid flow path, and the second filter element being disposed in the housing across a second fluid flow path; the housing including, in the cavity, an upstream inlet chamber between the upstream surfaces of the first and second filter elements and bordered by the inner surface of at least one side wall of the first and/or second section and the upstream surfaces of the filter elements, the upstream chamber being free of a solid partition between the inner surfaces of the first and second filter elements; the housing defining the first fluid flow path between the inlet, the upstream inlet chamber, the first filtrate downstream chamber and the outlet, wherein the first filter element is disposed across the first fluid flow path; and, defining the second fluid flow path between the inlet, the upstream inlet chamber, the second filtrate downstream chamber and the outlet, wherein the second filter element is disposed across the second fluid flow path.

In another embodiment, a filter device comprises a housing comprising a first section and a second section, the first section comprising a top wall comprising an outer surface and an inner surface, the first section including a first filtrate downstream chamber and a first vent chamber, the first filtrate downstream chamber including a portion of the inner surface of the top wall, and the first vent chamber including another portion of the inner surface of the top wall, the second section comprising a bottom wall comprising an outer surface and an inner surface, the second section including a second filtrate downstream chamber and a second vent chamber, the second filtrate downstream chamber including a portion of the inner surface of the bottom wall, and the second vent chamber including another portion of the inner surface of the bottom wall; the housing further comprising an inlet and an outlet, opposing first side walls and opposing second side walls, wherein the first and/or second housing sections comprise opposing first side walls having inner surfaces, and the first and/or second housing sections comprise opposing second side walls having inner surfaces, and the housing comprises a cavity bordered by the inner surfaces of the top, bottom, and side walls; a filter comprising at least first and second spaced apart porous filter elements, each filter element comprising a hydrophilic membrane, the first and second filter elements each having an upstream surface and a downstream surface, the first filter element being disposed in the housing across a first fluid flow path, and the second filter element being disposed in the housing across a second fluid flow path; the housing including, in the cavity, an upstream inlet chamber between the upstream surfaces of the first and second filter elements and bordered by the inner surfaces of the side walls and the upstream surfaces of the filter elements, the upstream chamber being free of a solid partition between the upstream surfaces of the first and second filter elements; the housing defining the first fluid flow path between the inlet, the upstream inlet chamber, the first filtrate downstream chamber and the outlet, wherein the first filter element is disposed across the first fluid flow path; and, defining the second fluid flow path between the inlet, the upstream inlet chamber, the second filtrate downstream chamber and the outlet, wherein the second filter element is disposed across the second fluid flow path.

Methods of priming the devices, and methods of using the devices to filter fluid, e.g., for administration to a subject, and systems including the devices, are also provided according to embodiments of the invention.

BRIEF DESCRIPTION OF THE SEVERAL VIEWS OF THE DRAWING(S)

FIGS. 1A and 1B are exploded views (top perspective view and bottom perspective view, respectively) of an embodiment of the filter device of the present invention, showing first and second housing sections, a filter comprising first and second filter elements, first and second filtrate downstream chambers, first and second vent elements, and first and second vent chambers.

FIG. 4 is a top plan view and a bottom plan view of another embodiment of the filter device, wherein the housing includes a clip.

FIGS. 5A and 5B are exploded views (top perspective view and bottom perspective view, respectively) of another embodiment of the filter device, wherein the center channel in the first and second filtrate downstream chambers is covered for most of the length of the channel.

FIGS. 6A and 6B are exploded views (top perspective view and bottom perspective view, respectively) of another embodiment of the filter device, wherein the first filtrate downstream chamber further comprises an inlet, and the second filtrate downstream chamber further comprises an outlet.

FIGS. 7A and 7B are exploded views (top perspective view and bottom perspective view, respectively) of another embodiment of the filter device, wherein the first filtrate downstream chamber includes a single vent.

FIGS. 8A and 8B are exploded views (top perspective view and bottom perspective view, respectively) of another embodiment of the filter device, wherein the second filtrate downstream chamber includes two vents.

FIGS. 9A and 9B are exploded views (top perspective view and bottom perspective view, respectively) of another embodiment of the filter device, wherein the device comprises three housing sections.

FIGS. 10A and 10B are exploded views (top perspective view and bottom perspective view, respectively) of another embodiment of the filter device, wherein a component of the outlet is attached to both the first housing section and the second housing section.

DETAILED DESCRIPTION OF THE INVENTION

Figure 2A:
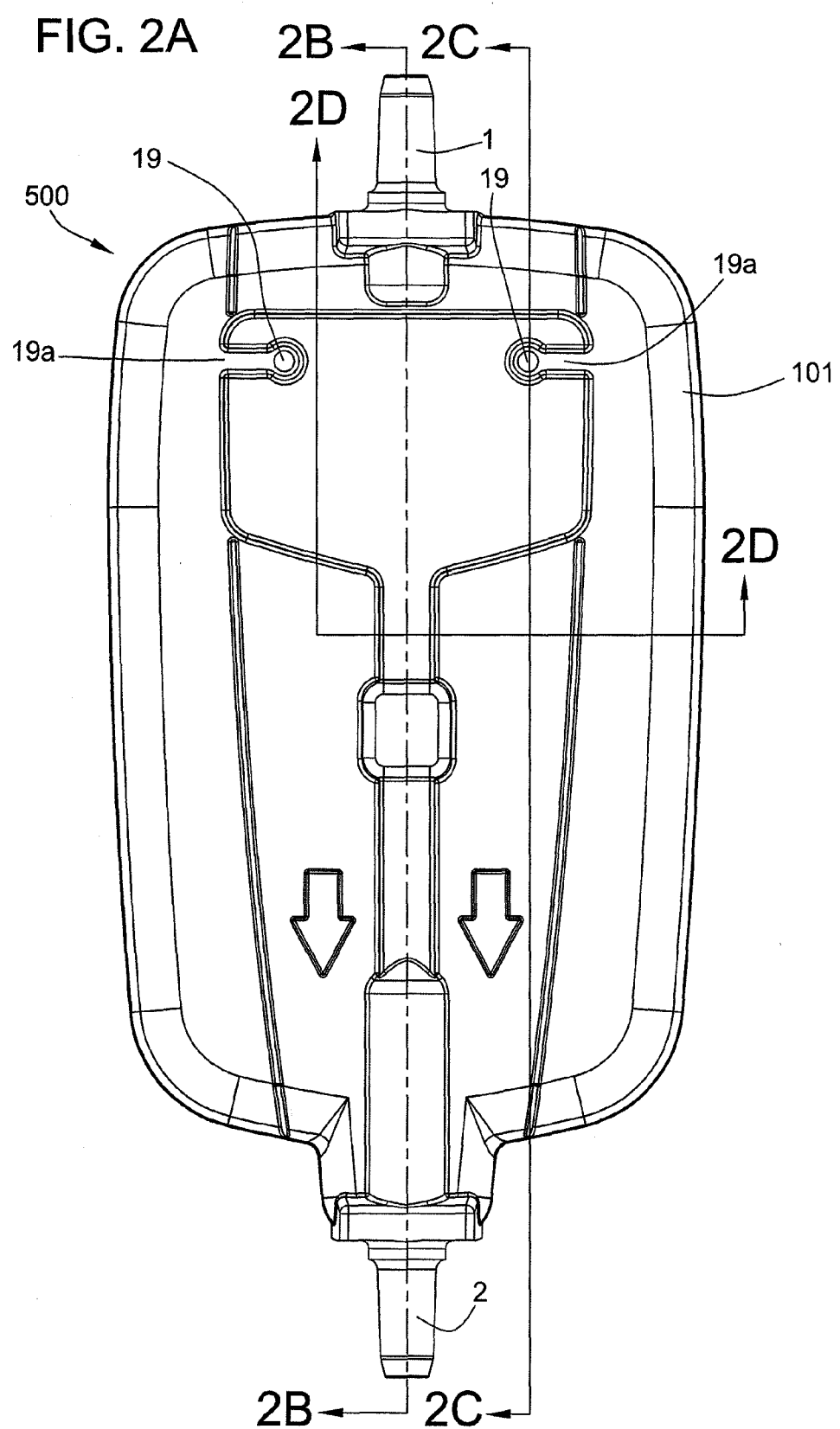
FIG. 2A is a top view of an embodiment of the filter device of the present invention.

An embodiment of the invention provides a filter device comprising a housing comprising at least a first section and a second section, (i) the first section comprising a top wall comprising an outer surface and an inner surface, the first section including a first filtrate downstream chamber, the first filtrate downstream chamber including a portion of the inner surface of the top wall, (ii) the second section comprising a bottom wall comprising an outer surface and an inner surface, the second section including a second filtrate downstream chamber, the second filtrate downstream chamber including a portion of the inner surface of the bottom wall; wherein the first section including the first filtrate downstream chamber also includes at least one first vent chamber, and the first vent chamber includes another portion of the inner surface of the top wall and/or wherein the second section including the second filtrate downstream chamber also includes at least one second vent chamber, and the second vent chamber includes another portion of the inner surface of the bottom wall; the housing further comprising an inlet, an outlet, at least one side wall having a side wall inner surface, and a cavity bordered by the inner surfaces of the top and bottom walls, and the inner surface of the at least one side wall; a filter comprising at least first and second spaced apart porous filter elements, each filter element comprising a porous hydrophilic membrane, the first and second filter elements each having an upstream surface and a downstream surface, the first filter element being disposed in the housing across a first fluid flow path, and the second filter element being disposed in the housing across a second fluid flow path; the housing including, in the cavity, an upstream inlet chamber between the upstream surfaces of the first and second filter elements and bordered by the inner surface of the at least one side wall and the upstream surfaces of the filter elements; the housing defining the first fluid flow path between the inlet, the upstream inlet chamber, the first filtrate downstream chamber and the outlet, wherein the first filter element is disposed across the first fluid flow path; and, defining the second fluid flow path between the inlet, the upstream inlet chamber, the second filtrate downstream chamber and the outlet, wherein the second filter element is disposed across the second fluid flow path.

In preferred embodiments of the device, the upstream inlet chamber is free of a solid partition between the upstream surfaces of the first and second filter elements and/or at least a portion of the top wall of the first filtrate downstream chamber and at least a portion of the bottom wall of the second filtrate downstream chamber is transparent or translucent.

In more preferred embodiments of the device, the top wall inner surface of the first filtrate downstream chamber and the bottom wall inner surface of the second filtrate downstream chamber each comprise a plurality of ridges providing a plurality of channels, the channels directing fluid from the downstream surfaces of the first and second filter elements to the housing outlet.

Preferably, the first and/or the second vent chamber further comprises a vent port and a vent including a first microporous vent element arranged to allow gas to pass (e.g., from the upstream inlet chamber) through the vent element and the vent port.

In some embodiments of the device, the first section including the first filtrate downstream chamber includes two first vent chambers, and the two first vent chambers each include separate portions of the inner surface of the top wall and/or the second section including the second filtrate downstream chamber includes two second vent chambers, and the two second vent chambers each include separate portions of the inner surface of the bottom wall.

Alternatively, or additionally, an embodiment, the device further comprises central channels in the first and/or second filtrate downstream chambers that are covered for most of the length of the channels.

In some embodiments of the device, the first and/or second housing sections comprise the at least one side wall having the side wall inner surface. For example, the housing can comprise opposing first side walls having first side wall inner surfaces, and opposing second side walls having second side wall inner surfaces, wherein the housing comprises the cavity bordered by the inner surfaces of the top, bottom, and side walls; and the first and/or the second housing sections comprise the opposing first side walls having the first side wall inner surfaces, and the first and/or the second housing sections comprise the opposing second side walls having the second side wall inner surfaces. Typically, the opposing first side walls are substantially parallel to each other and the opposing second side walls are substantially parallel to each other.

In another embodiment of the device, the housing further comprises a third housing section, the third section comprising the at least one side wall having the side wall inner surface. For example, the housing can comprise opposing first side walls having first side wall inner surfaces, and opposing second side walls having second side wall inner surfaces, wherein the housing comprises the cavity bordered by the inner surfaces of the top, bottom, and side walls; and the third section comprises the opposing first side walls having the first side wall inner surfaces, and the opposing second side walls having the second side wall inner surfaces.

A filter device according to yet another embodiment of the invention comprises a housing comprising at least a first section and a second section, the first section comprising a top wall comprising an outer surface and an inner surface, the first section including a first filtrate downstream chamber, the first filtrate downstream chamber including a portion of the inner surface of the top wall; the second section comprising a bottom wall comprising an outer surface and an inner surface, the second section including a second filtrate downstream chamber, the second filtrate downstream chamber including a portion of the inner surface of the bottom wall; wherein the first section including the first filtrate downstream chamber also includes at least one first vent chamber, and the first vent chamber includes another portion of the inner surface of the top wall and/or wherein the second section including the second filtrate downstream chamber also includes at least one second vent chamber, and the second vent chamber includes another portion of the inner surface of the bottom wall; the housing further comprising an inlet and an outlet, opposing first side walls having first side wall inner surfaces, and opposing second side walls having second side wall inner surfaces, and the housing comprises a cavity bordered by the inner surfaces of the top, bottom, and side walls; a filter comprising at least first and second spaced apart porous filter elements, each filter element comprising a hydrophilic membrane, the first and second filter elements each having an upstream surface and a downstream surface, the first filter element being disposed in the housing across a first fluid flow path, and the second filter element being disposed in the housing across a second fluid flow path; the housing including, in the cavity, an upstream inlet chamber between the upstream surfaces of the first and second filter elements and bordered by the inner surfaces of the side walls and the upstream surfaces of the filter element, the upstream chamber being free of a solid partition between the inner surfaces of the first and second filter elements; the housing defining the first fluid flow path between the inlet, the upstream inlet chamber, the first filtrate downstream chamber and the outlet, wherein the first filter element is disposed across the first fluid flow path; and, defining the second fluid flow path between the inlet, the upstream inlet chamber, the second filtrate downstream chamber and the outlet, wherein the second filter element is disposed across the second fluid flow path.

In still another embodiment, a filter device is provided comprising a housing comprising a first section and a second section, (i) the first section comprising a top wall comprising an outer surface and an inner surface, and at least one side wall, the first section including a first filtrate downstream chamber, the first filtrate downstream chamber including a portion of the inner surface of the top wall, (ii) the second section comprising a bottom wall comprising an outer surface and an inner surface, and at least one side wall, the second section including a second filtrate downstream chamber, the second filtrate downstream chamber including a portion of the inner surface of the bottom wall, wherein the first section including the first filtrate downstream chamber also includes at least one first vent chamber, and the first vent chamber includes another portion of the inner surface of the top wall and/or wherein the second section including the second filtrate downstream chamber also includes at least one second vent chamber, and the second vent chamber includes another portion of the inner surface of the bottom wall; the housing further comprising an inlet and an outlet, and a cavity bordered by the inner surfaces of the top and bottom walls, and an inner surface of at least one side wall of the first and/or second section; a filter comprising at least first and second spaced apart porous filter elements, each element comprising a hydrophilic membrane, the first and second filter elements each having an upstream surface and a downstream surface, the first filter element being disposed in the housing across a first fluid flow path, and the second filter element being disposed in the housing across a second fluid flow path; the housing including, in the cavity, an upstream inlet chamber between the inner surfaces of the first and second filter elements and bordered by the inner surface of at least one side wall of the first and/or second section and the upstream surfaces of the filter elements; the housing defining the first fluid flow path between the inlet, the upstream inlet chamber, the first filtrate downstream chamber and the outlet, wherein the first filter element is disposed across the first fluid flow path; and, defining the second fluid flow path between the inlet, the upstream inlet chamber, the second filtrate downstream chamber and the outlet, wherein the second filter element is disposed across the second fluid flow path.

Yet another embodiment comprises a filter device comprising a housing comprising a first section and a second section, (i) the first section comprising a top wall comprising an outer surface and an inner surface, and at least one side wall, the first section including a first filtrate downstream chamber, the first filtrate downstream chamber including a portion of the inner surface of the top wall, (ii) the second section comprising a bottom wall comprising an outer surface and an inner surface, and at least one side wall, the second section including a second filtrate downstream chamber, the second filtrate downstream chamber including a portion of the inner surface of the bottom wall; the housing further comprising an inlet and an outlet, and a cavity bordered by the inner surfaces of the top and bottom walls, and an inner surface of at least one side wall of the first and/or second section; a filter comprising at least first and second spaced apart porous filter elements, each filter element comprising a hydrophilic membrane, the first and second filter elements each having an upstream surface and a downstream surface, the first filter element being disposed in the housing across a first fluid flow path, and the second filter element being disposed in the housing across a second fluid flow path; the housing including, in the cavity, an upstream inlet chamber between the upstream surfaces of the first and second filter elements and bordered by the inner surface of at least one side wall of the first and/or second section and the upstream surfaces of the filter elements; the housing defining the first fluid flow path between the inlet, the upstream inlet chamber, the first filtrate downstream chamber and the outlet, wherein the first filter element is disposed across the first fluid flow path; and, defining the second fluid flow path between the inlet, the upstream inlet chamber, the second filtrate downstream chamber and the outlet, wherein the second filter element is disposed across the second fluid flow path; wherein the top wall inner surface of the first filtrate downstream chamber and the bottom wall inner surface of the second filtrate downstream chamber each comprise a plurality of ridges providing a plurality of channels, the channels directing fluid from the downstream surfaces of the first and second filter elements to the housing outlet and wherein the top wall inner surface of the first filtrate downstream chamber and the bottom wall inner surface of the second filtrate downstream chamber each comprise a central channel that is wider and/or deeper than the other channels, and, wherein each central channel has side, top, and bottom walls forming a closed tube for at least a majority of the length of each central channel. In a more preferred embodiment, the first section including a first filtrate downstream chamber also comprises a first vent chamber, the first vent chamber including another portion of the inner surface of the top wall, and the second section including a second filtrate downstream chamber also comprises a second vent chamber, the second vent chamber including another portion of the inner surface of the bottom wall.

In accordance with another embodiment of the present invention, a filter device is provided comprising a housing comprising a first section and a second section, (i) the first section comprising a top wall comprising an outer surface and an inner surface, and at least one side wall, the first section including a first filtrate downstream chamber and a first vent chamber, the first filtrate downstream chamber including a portion of the inner surface of the top wall, and the first vent chamber including another portion of the inner surface of the top wall, (ii) the second section comprising a bottom wall comprising an outer surface and an inner surface, and at least one side wall, the second section including a second filtrate downstream chamber and a second vent chamber, the second filtrate downstream chamber including a portion of the inner surface of the bottom wall, and the second vent chamber including another portion of the inner surface of the bottom wall; the housing further comprising an inlet and an outlet, and a cavity bordered by the inner surfaces of the top and bottom walls, and an inner surface of at least one side wall of the first and/or second section; a filter comprising at least first and second spaced apart porous filter elements, each filter element comprising a hydrophilic membrane, the first and second filter elements each having an upstream surface and a downstream surface, the first filter element being disposed in the housing across a first fluid flow path, and the second filter element being disposed in the housing across a second fluid flow path; the housing including, in the cavity, an upstream inlet chamber between the upstream surfaces of the first and second filter elements and bordered by the inner surface of at least one side wall of the first and/or second section and the upstream surfaces of the filter elements, the upstream chamber being free of a solid partition between the inner surfaces of the first and second filter elements; the housing defining the first fluid flow path between the inlet, the upstream inlet chamber, the first filtrate downstream chamber and the outlet, wherein the first filter element is disposed across the first fluid flow path; and, defining the second fluid flow path between the inlet, the upstream inlet chamber, the second filtrate downstream chamber and the outlet, wherein the second filter element is disposed across the second fluid flow path.

In another embodiment, a filter device comprises a housing comprising a first section and a second section, the first section comprising a top wall comprising an outer surface and an inner surface, the first section including a first filtrate downstream chamber and a first vent chamber, the first filtrate downstream chamber including a portion of the inner surface of the top wall, and the first vent chamber including another portion of the inner surface of the top wall, the second section comprising a bottom wall comprising an outer surface and an inner surface, the second section including a second filtrate downstream chamber and a second vent chamber, the second filtrate downstream chamber including a portion of the inner surface of the bottom wall, and the second vent chamber including another portion of the inner surface of the bottom wall; the housing further comprising an inlet and an outlet, opposing first side walls and opposing second side walls, wherein the first and/or second housing sections comprise opposing first side walls having inner surfaces, and the first and/or second housing sections comprise opposing second side walls having inner surfaces, and the housing comprises a cavity bordered by the inner surfaces of the top, bottom, and side walls; a filter comprising at least first and second spaced apart porous filter elements, each filter element comprising a hydrophilic membrane, the first and second filter elements each having an upstream surface and a downstream surface, the first filter element being disposed in the housing across a first fluid flow path, and the second filter element being disposed in the housing across a second fluid flow path; the housing including, in the cavity, an upstream inlet chamber between the upstream surfaces of the first and second filter elements and bordered by the inner surfaces of the side walls and the upstream surfaces of the filter elements, the upstream chamber being free of a solid partition between the inner surfaces of the first and second filter elements; the housing defining the first fluid flow path between the inlet, the upstream inlet chamber, the first filtrate downstream chamber and the outlet, wherein the first filter element is disposed across the first fluid flow path; and, defining the second fluid flow path between the inlet, the upstream inlet chamber, the second filtrate downstream chamber and the outlet, wherein the second filter element is disposed across the second fluid flow path.

Advantageously, "inside-out" filter devices according to the invention can be assembled with a reduced number of components (e.g., housing elements and/or fewer vents) as compared to dual filter element "outside-in" IV filter devices. Preferably, filter devices according to embodiments of the invention comprise housings allowing the user to view the outlet chambers. Another advantage of those "inside-out" filter devices according to the invention that further comprise one or more vents, as compared to dual filter element "outside-in" IV filter devices, is that proper priming can be more easily verified. Such vented devices according to the invention preferably self-prime or auto-prime, i.e., the device does not need to be inverted during filling, e.g., if desired, the device can be hung vertically with the inlet positioned upwardly and the outlet positioned downwardly.

An embodiment of a method according to the invention comprises passing a fluid through an embodiment of the filter device. For example, one embodiment of the method comprises passing a fluid, such as an IV fluid, through the inlet into the inlet chamber, passing some of the fluid along a first fluid flow path through a first filter element through a first filtrate downstream chamber and through the outlet, passing some of the fluid along a second fluid flow path through a second filter element through a second filtrate downstream chamber and through the outlet, and passing air or gas from the inlet chamber through at least one vent. In a preferred embodiment of the method, the method further comprises passing filtered IV fluid through the outlet to a subject, such as a patient.

A variety of fluids, preferably, IV fluids, can be filtered in accordance with filter devices, methods, and systems according to the invention. Suitable fluids are known in the art. Typically, the fluid is a physiologically acceptable fluid, and can be a sterile fluid. A plurality of fluids can used in accordance with the invention, and the fluids can be compatible with one another. For example, one fluid can be used to prime the device before administering another fluid, such as a fluid comprising a drug and/or a nutrient. The fluids can be commingled and/or mixed, if desired.

Embodiments of the device are suitable for a variety of applications, including passing fluid(s) to any subject such as a patient, e.g., embodiments of the device are suitable for administration of fluid(s) to humans, and to animals. Embodiments of the device are suitable for use in, for example, applications involving apheresis. An embodiment of a system according to the invention comprises an embodiment of the device, at least one conduit (preferably, at least two conduits), and at least one container for holding a fluid to be filtered, preferably, wherein the container comprises a flexible container, e.g., wherein the container is placed in fluid communication with the device inlet via a first conduit, and a second conduit communicates with the device outlet.

The housing can be any suitable shape, e.g., generally rectangular, square, circular, oval, or triangular. The housing can be configured for ease of use and/or for subject comfort. For example, the housing can include one or more of the following: the inlet and outlet on the same housing section wherein a housing section without the inlet and outlet is placed in contact with the subject or the patient's clothing, a bracket, a clip, and/or an eyelet for attachment to clothing, bedding, and/or another structure, e.g., for support or ease of fluid administration.

The housing can be sealed as is known in the art, utilizing, for example, an interference fit, an adhesive, a solvent, laser welding, radio frequency sealing, ultrasonic sealing and/or heat sealing. Additionally, or alternatively, the housing can be sealed via injection molding. The filter and vent elements can be sealed within the housing as is known in the art, e.g., via compression, interference fit, or bonded and/or welded to the housing.

The housing can be fabricated from any suitable rigid impervious material, including any impervious thermoplastic material, which is compatible with the fluid being processed. In a preferred embodiment, the housing is a polymer, more preferably a transparent or translucent polymer, such as an acrylic, polypropylene, polystyrene, or a polycarbonated resin. Such a housing is easily and economically fabricated, and allows observation of the passage of fluid through the housing. If desired, the housing can be fabricated such that one or more desired portions (and/or entire housing sections) are transparent or translucent.

Typically, the housing comprises a first housing section and a second housing section, and in some embodiments, the housing comprises first, second, and third, housing sections.

The housing includes a cavity, bordered by the inner surfaces of the top and bottom walls, and by the inner surface of at least one side wall.

Each of the components of the invention will now be described in more detail below, wherein like components have like reference numbers.

Using the embodiments shown in FIGS. 1, 2, 5-8, and 10 for reference, the illustrated filter device 500 comprises a housing 200 comprising a first section 101 and a second section 102, and a filter 50 comprising spaced apart first and second porous filter elements 51', 52', the first filter element 51' comprising a first hydrophilic microporous membrane 51, the second filter element 52' comprising a second hydrophilic microporous membrane 52, sealed in the housing. The filter 50 is disposed in a cavity formed in the housing (FIG. 2B shows cavity 40). In the embodiments illustrated in FIGS. 1, 2, 4, 5, 7, 8, and 10, first section 101 includes an inlet 1 and an outlet 2.

In other embodiments, the inlet and outlet can be associated with different sections of the housing (e.g., as shown in FIG. 6), or with an additional (third) housing section (e.g., as shown in FIG. 9), or the second section can include the inlet and outlet (not shown). In some embodiments wherein the device is in contact with the subject during use, it may be desirable to have the inlet and outlet associated with the same housing section, wherein a housing section without the inlet and the outlet is placed in contact with the subject.

As shown in more detail in FIGS. 1(A-B), 5(A-B), and 10(A-B), in these illustrated embodiments, the first section 101 comprises a top wall 110 comprising an outer surface 110a and an inner surface 110b, and includes a first filtrate downstream chamber 10 and a first vent chamber 15, the first filtrate downstream chamber 10 including a portion 16 of the inner surface of the top wall, and the first vent chamber 15 including another portion 18 of the inner surface of the top wall, and the second section 102 comprises a bottom wall 120 comprising an outer surface 120a and an inner surface 120b, and includes a second filtrate downstream chamber 20 and a second vent chamber 25, the second filtrate downstream chamber 20 including a portion 26 of the inner surface of the bottom wall, and the second vent chamber 25 including another portion 28 of the inner surface of the bottom wall. Other configurations, including other arrangements and numbers and/or locations of vent chambers, are encompassed by embodiments of the invention, e.g., as shown in FIGS. 6(A-B), 7(A-B), 8(A-B), and 9(A-B).

The illustrated first and second sections shown in FIGS. 1(A-B), 5(A-B), 6(A-B), 7(A-B), 8(A-B), and 10(A-B), each include at least one side wall, wherein the side wall of at least one section has an inner surface and an outer surface. In some embodiments wherein the housing is generally square (not shown) or generally rectangular (e.g., as shown in FIGS. 2, 5-8, and 10), the first housing section 101 comprises opposing first side walls 115 and opposing second side walls 115', each side wall comprising an outer surface 115a (for side wall 115), 115'a (for side wall 115') and an inner surface 115b (for side wall 115), 115'b (for side wall 115'), and the second housing section 102 comprises opposing first side walls 125 and opposing second side walls 125', each side wall comprising an outer surface 125a (for side wall 125), 125'a (for side wall 125') and a cavity 40 (see FIG. 2B) bordered by the inner surfaces of the top and bottom walls as well as the inner surfaces of the first housing section side walls. In the embodiment illustrated in FIG. 1(A-B), the first housing section 101 further comprises a tongue 118 (illustrated as extending from the side walls 115 and 115', respectively, such that a portion of inner surfaces 115b and 115'b each form a portion of tongue inner surfaces 118b and 118'b, respectively, and a portion of outer surfaces 115a and 115'a each form a portion of tongue outer surfaces 118a and 118'a, respectively), and the second housing section 102 further comprises side wall inner surfaces 125b (for side wall 125), and 125'b (for side wall 125'), and a groove 128 for engaging the tongue. In these illustrated embodiments, the fitting of the first and second housing sections 101 and 102 together is such that the side walls of the second section 102 do not provide inner surfaces bordering the cavity 40. However, the invention is not limited to such configurations, e.g., the first and housing sections can each include inner surfaces projecting upwardly to provide part of the inner surfaces bordering the cavity.

Alternatively, in some embodiments the housing does not have substantially parallel opposing side walls, e.g., in some embodiments wherein the housing is generally round or oval (not shown) the housing sections can each comprise at least one side wall, and in some embodiments wherein the housing is generally triangular (not shown) the housing sections can each comprise at least three side walls, wherein the inner surface(s) of at least one of the side wall(s) and the inner surfaces of the top and bottom walls border the cavity. Additionally, or alternatively, the device can comprise first, second, and third housing sections (e.g., as shown in FIG. 9(A-B)), wherein the third section is between the first and second sections, and the third section provides the side wall(s) bordering the cavity.

In the embodiments illustrated in FIGS. 1, 2, and 5-8, and 10, the filter 50 comprising spaced apart first and second porous filter elements 51', 52' comprising first and second hydrophilic microporous membranes 51, 52, is disposed in the cavity 40 of the housing, wherein the first and second filter elements 51', 52', each have an downstream (or outer) surface 51a, 52a and an upstream (or inner) surface 51b, 52b. In those embodiments wherein each filter element is a hydrophilic microporous membrane, the downstream surface of each filter element is the downstream surface of the each membrane, and the upstream surface of each filter element is the upstream surface of the each membrane. In other embodiments wherein the filter further comprises additional filter elements (in addition to the first and second hydrophilic membranes, not shown), e.g., an upstream fibrous prefilter and/or a downstream support such as a fibrous element or a mesh or a screen, the downstream surface of each filter element can be the downstream surface of the each support and/or the upstream surface of each filter element can be the upstream surface of the each fibrous prefilter.

The upstream inlet chamber 5 is located between the upstream surfaces 51b, 52b of the first and second filter elements 51', 52' (for convenience, the following discussion will refer to 51b and 52b as the upstream surfaces of the membranes, though the upstream surfaces can be fibrous media as discussed above) and bordered by the upstream surfaces of the membranes and the inner surfaces of the side walls (which may include the inner surfaces of a tongue) of the first section of the housing. In the embodiment illustrated in FIG. 9, the upstream inlet chamber is located between the upstream surfaces of the first and second membranes and bordered by the inner surfaces of the side walls of the third section of the housing and the upstream surfaces of the membranes. In each of these illustrated embodiments, the illustrated upstream chamber is free of a solid partition between the upstream surfaces of the first and second membranes.

Figure 2B:
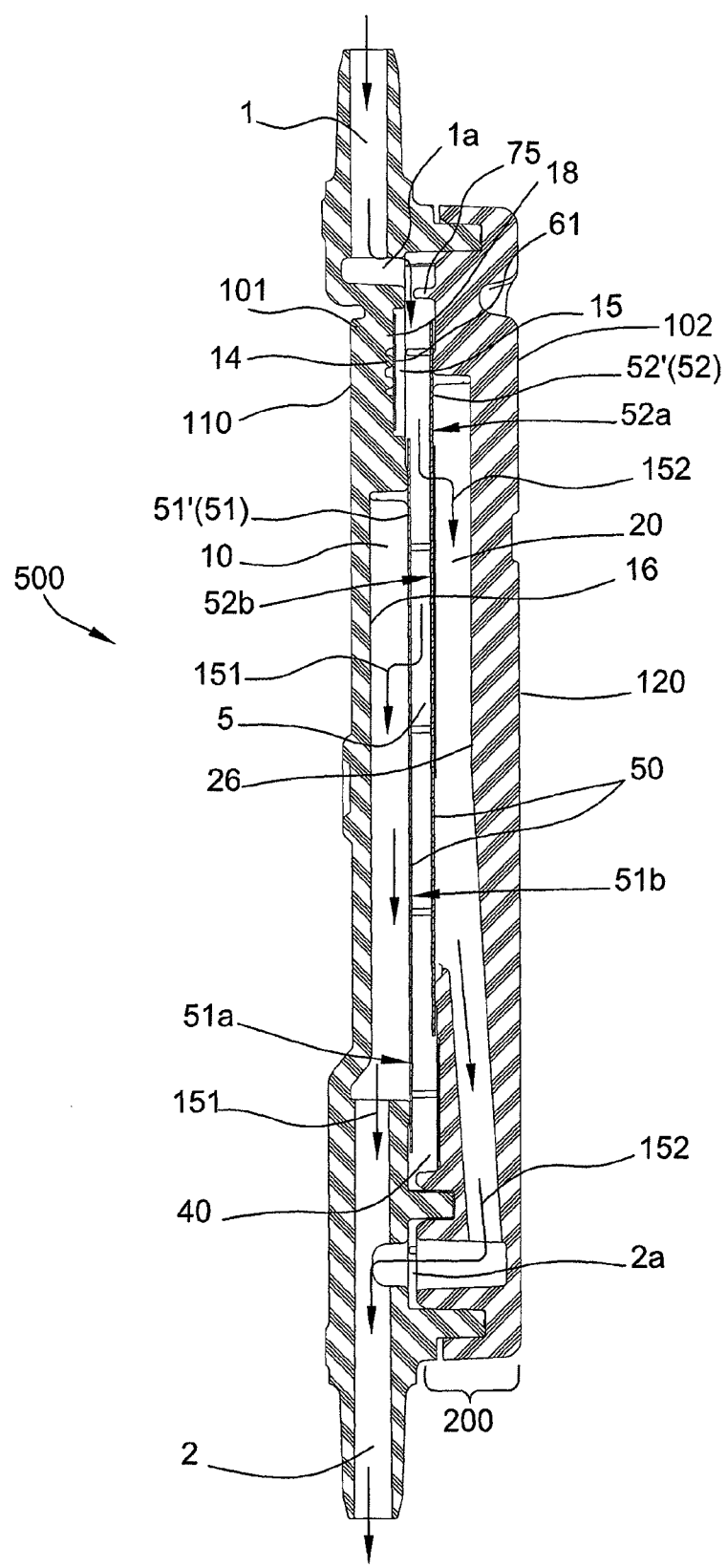
FIG. 2B is a cross-sectional side view along line 2B-2B of the device shown in FIG. 2A.
Figure 2C:
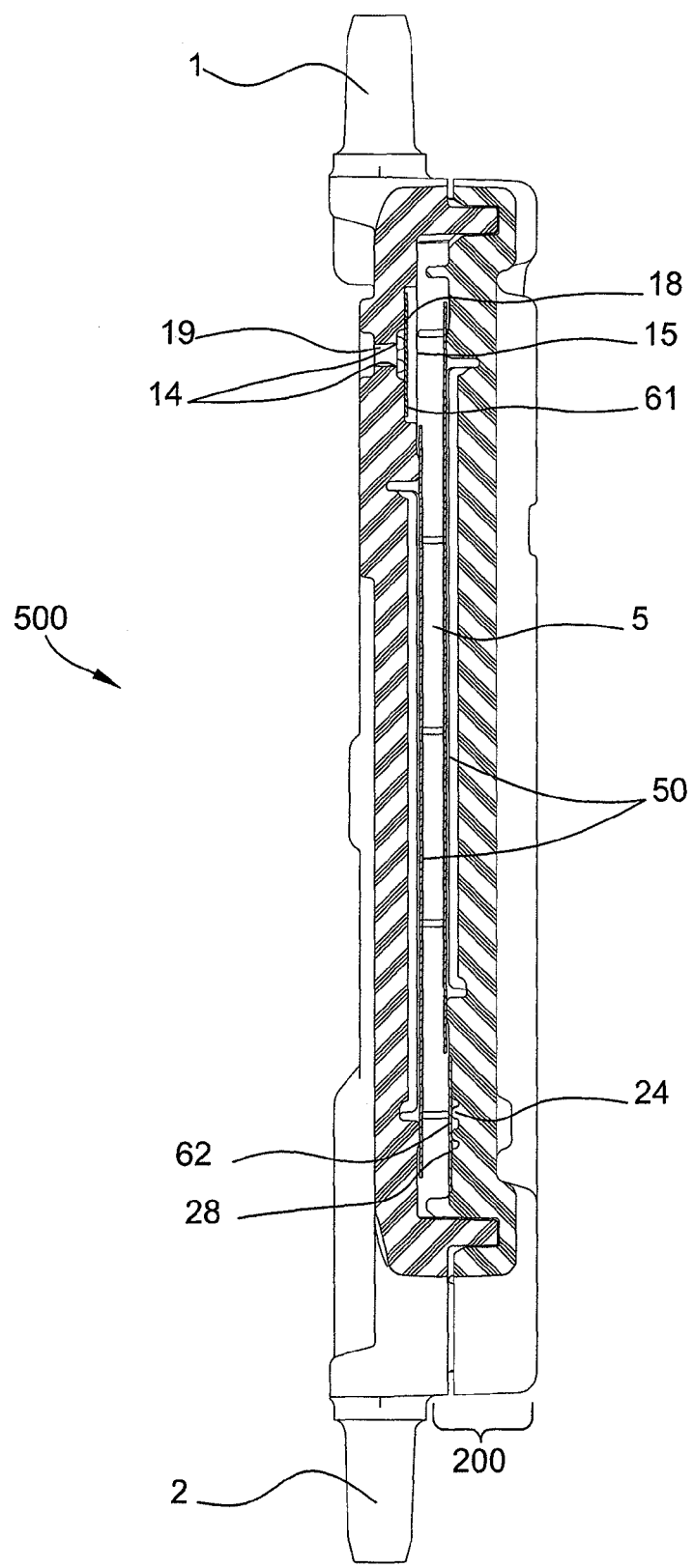
FIG. 2C is a sectional view along line 2C-2C of the device shown in FIG. 2A.

Using the cross-sectional view in FIG. 2B for reference (and as is applicable to embodiments wherein the housing has three sections and/or the inlet and outlet associated with different housing sections), the first and second filter elements are disposed in the housing 200, and the housing defines a first fluid flow path 151 between the inlet 1, inlet passageway 1a, the upstream inlet chamber 5, the first filtrate downstream chamber 10, and the outlet 2, wherein the first filter element 51' (illustrated as membrane 51) is disposed across the first fluid flow path 151; and, defines the second fluid flow path 152 between the inlet 1, inlet passageway 1a, the upstream inlet chamber 5, the second filtrate downstream chamber 20, the outlet passageway 2a, and the outlet 2, wherein the second filter element 52' (illustrated as membrane 52) is disposed across the second fluid flow path 152. FIGS. 1A, 2B, and 5A, in particular, also show an optional flow baffle 75, downstream of inlet passageway 1a and adjacent the entrance to the upstream inlet chamber 5. In some embodiments, the flow baffle may deflect liquid flow (e.g., toward the sides of the sides of the inlet chamber 5) and improve the priming efficiency of the device.

Preferably, the filter device comprises one or more vents, wherein the first housing section and/or the second housing section includes the vent(s), preferably wherein the vent comprises a hydrophobic microporous vent element and a vent port, more preferably, wherein a portion of the inner surface of the housing section (other than the portion of the inner surface forming a wall of a filtrate downstream chamber) comprises a wall of the vent chamber, even more preferably wherein the vent chamber comprises a plurality of ridges providing at least one channel directing air or gas from the downstream surfaces of the vent elements through the vent ports in the housing. For example, the embodiment shown in FIG. 7 comprises a single vent, wherein the first housing section comprising the first filtrate downstream chamber comprises the vent.

In those embodiments wherein the device comprises at least two vents, the first housing section can include two or more vents and/or the second housing section can include two or more vents (e.g., as shown in FIG. 8). More preferably, the first and second housing sections each comprise one or more vents (e.g., as shown in FIGS. 1, 5, 6, 9, and 10), each vent comprising a hydrophobic microporous vent element and a vent port, allowing gas or air to be separated from the liquid flow path and passed from the device. FIGS. 1B and 5B show first vent chambers 15, wherein the first vent chambers each further comprise a first vent port 19 and a first vent microporous hydrophobic membrane 61 arranged to allow gas to pass through the first vent membrane and the first vent port of the first vent chamber. FIGS. 1A and 5A show second vent chamber 25, wherein the second vent chamber further comprises one or more second vent ports 29, and a second vent microporous hydrophobic membrane 62 arranged to allow gas to pass through the second vent element and the second vent port(s) of the second vent chamber. FIGS. 6-10 also show first vents, and the embodiments shown in FIGS. 6 and 8-10 also show second vents, each vent comprising a vent chamber, vent port, and a vent microporous hydrophobic membrane. In those embodiments wherein the outer surface of a wall of the device housing includes a recessed vent port, the outer surface of the wall preferably also includes at least one vent slot. For example, in the embodiments illustrated in FIGS. 1B and 5B, vent ports 29 are recessed from the external surface of peripheral ridge 126, and the peripheral ridge includes vent slots 29a. Such an arrangement may provide more efficient venting when that side of the housing is placed near, or in contact with, a patient's skin and/or clothing and/or when the housing is taped to the patient and tape may block the vent port(s). In the embodiments illustrated in FIGS. 1A and 5A, vent slots 19a each provide a channel having one end near or in vent port 19.

In the illustrated embodiments shown in FIGS. 1A, 1B, 5A, and 5B in particular (and also shown in some other illustrated embodiments), at least a portion 16 of the inner surface 110b of the first housing section comprising the top wall 110 of the first filtrate downstream chamber 10 and at least a portion 26 of the inner surface 120b of the second housing section comprising the bottom wall 120 of the second filtrate downstream chamber 20 each comprise a plurality of ridges 11 (first downstream chamber), 12 (second downstream chamber) providing a plurality of channels 11a, 12a, the channels directing fluid passing from the downstream surfaces of the first and second membranes to the device outlet passageway 2a and outlet 2. Typically, at least some of the ridges support the downstream surfaces of the filter elements (the illustrated downstream surfaces being shown as membranes) against liquid pressure while preventing the downstream surfaces from blocking the channels.

Similarly, as is also shown in FIGS. 1A, 1B, 5A, and 5B in particular (and also shown in some other illustrated embodiments), at least one other portion 18 of the inner surface 110a of the first housing section comprising the top wall 110 of the first vent chamber 15, and at least one other portion 28 of the inner surface of the second housing section 120 comprising the bottom wall 120 of the second vent chamber 25 each optionally comprise a plurality of ridges 14, 24 providing at least one channel 14a, 24a directing gas from the downstream surfaces of the vent elements through the vent ports in the housing. In some embodiments wherein the vent chambers include ridges, at least some of the ridges can support the downstream surfaces of the vent elements against liquid pressure while preventing the downstream surfaces from blocking the channels.

Preferably, the inner surfaces of the top and bottom walls of the filtrate chambers each comprise three or more channels, optionally wherein at least one channel associated with the top wall and at least one channel associated with the bottom wall has a greater depth and/or width than at least two other channels associated with the top and bottom walls and arranged substantially parallel thereto. In some embodiments, such an arrangement promotes more efficient filtrate flow to the outlet. In the optional embodiments shown in FIGS. 1(A-B) and 5(A-B), the central channel 11b, 12b in each filtrate chamber has a greater depth and width than the other channels in the respective filtrate chamber. Optionally, as is also shown in FIG. 2D, the tops of the ridges forming the central channel in the first and second housing channels are formed to include a raised bead 11f, 12f for sealing to the downstream surfaces of the filter elements.

Figure 3:
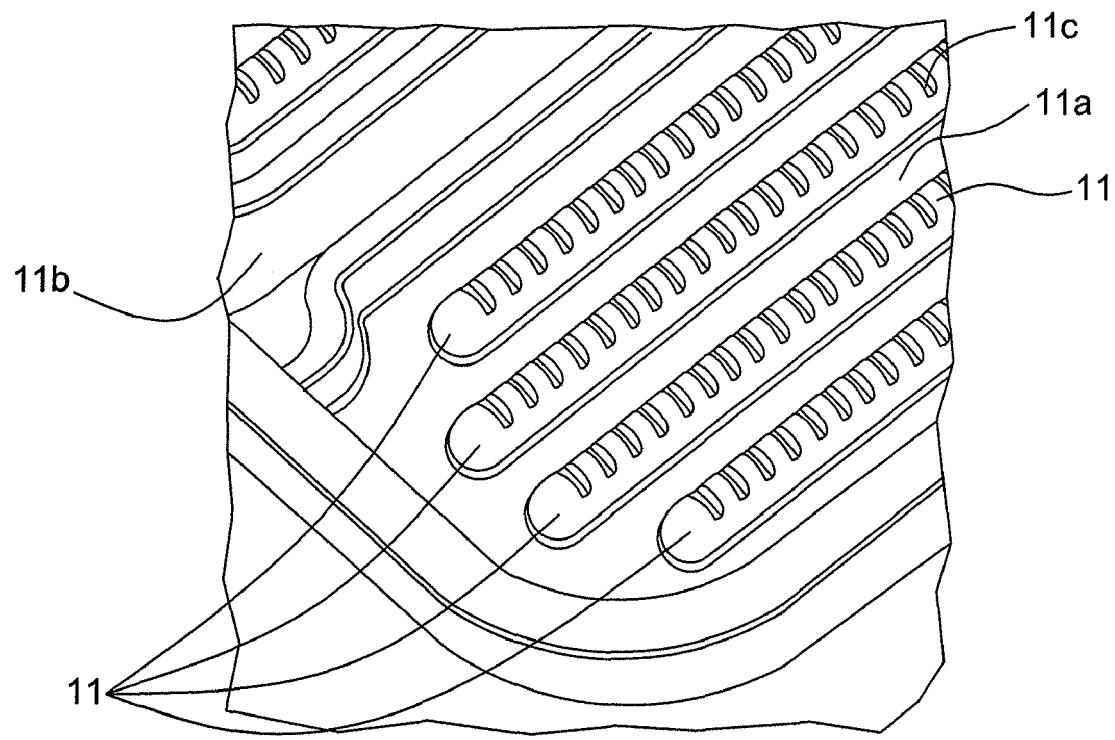
FIG. 3 shows a partial view of a downstream wall of a first filtrate chamber according to an embodiment of a filter device according to the present invention.

In another optional arrangement, as shown in FIG. 3, at least some of the ridges 11, 12 include grooves 11c, 12c angled or generally perpendicular to the channels. In some embodiments, such an arrangement may provide more effective filtration surface area, e.g., by contacting less of the downstream surface area of the filter elements and reducing blinding.

Figure 2D:
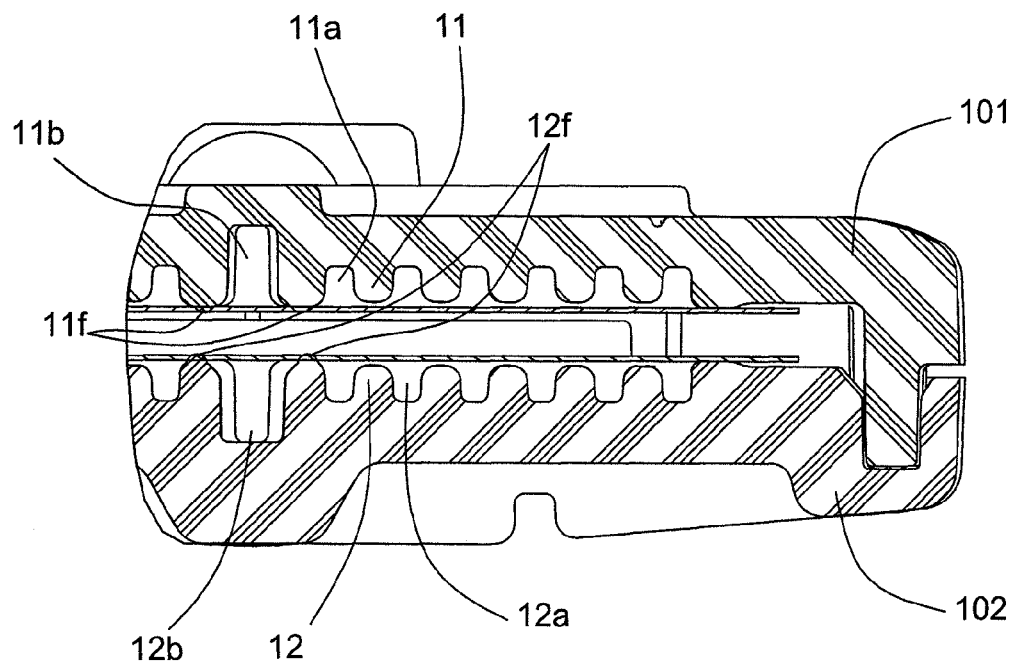
FIG. 2D is a sectional view along line 2D-2D of the device shown in FIG. 2A.
Figure 5C:
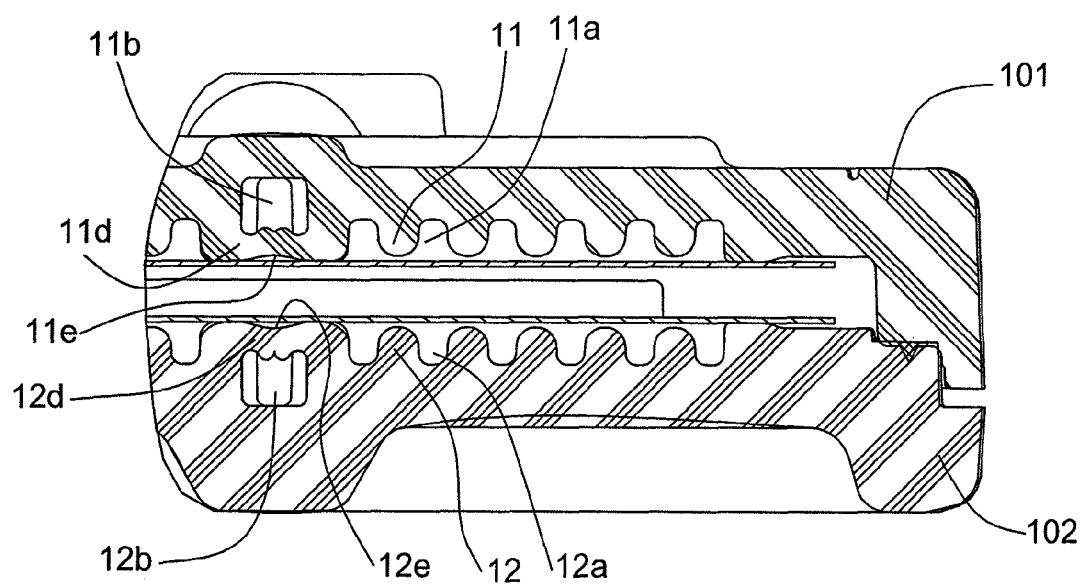
FIG. 5C is a sectional view along line 5C-5C of the device shown in FIGS. 5A and 5B when assembled.

The embodiment of a filter device shown in FIGS. 5A-B is generally similar to the embodiment shown in FIGS. 1A-B; however, in the embodiment shown in FIGS. 5A and 5B, the central channel 11b, 12b in each filtrate chamber is covered by channel wall 11d, 12d for a major portion (more preferably, at least about 60%) of the channel length such that the solid side, bottom, and top walls form a tube-like structure (FIGS. 2D and 5C show cross-sectional views of the respective central channels). For example, the channel wall can cover at least about 60% of the length, and in the illustrated embodiment, at least about 90% of the length, more preferably, providing a sealed tube with an opening where the fluid enters the channel and sealing the rest of the length of the tube. In some embodiments, such an arrangement can provide for separating air from the liquid more efficiently before the liquid flows through the channel. In the embodiment shown in FIG. 5C, the surface of the channel wall 11d, 12d facing the downstream surface of the membrane has a slight central depression 11e, 12e, along part of the length of the wall, running generally parallel to the other channels.

As noted above, the embodiment shown in FIG. 2D, optionally, the tops of the ridges forming the central channel in the first and second housing channels are formed to include a raised bead 11f, 12f for sealing to the downstream surfaces of the filter elements. Sealing the ridges forming the central channel in the first and second housing channels to the downstream surfaces of the filter elements can also provide a tube-like structure for priming and separating air from the liquid more efficiently before the liquid flows through the channel.

The inlet and outlet can be associated with the same housing sections (e.g., as shown in FIGS. 1, 4, 5, and 7-10) or different housing sections (e.g., as shown in FIG. 6). Alternatively, or additionally, a housing section can include an integrally attached inlet and/or outlet (e.g., the housing is formed including the inlet and/or outlet as shown in FIGS. 1, 5, and 7-9). A housing section can further comprise a separately attachable inlet and/or outlet (e.g., as shown in FIG. 10; showing a component of the outlet attached to both the first and the second housing sections), or the housing can include a combination of arrangements. For example, a housing section can include an integrally attached inlet (or outlet) and the housing section, or a different housing section, can further comprise a separately attachable outlet (or inlet).

While the inlet and outlet of many of the illustrated filter device are shown as male connectors, the invention is not so limited, and, for example, FIG. 4 shows an inlet comprising a female connector. A variety of connectors, including male and female connectors, including luer fittings (FIG. 4 shows an inlet comprising a luer fitting), are suitable and are known in the art.

Embodiments of the filter device can include additional structures, for example, one or more of a bracket, clip, and/or eyelet for attachment to clothing, bedding, and/or another structure, e.g., for support or ease of fluid administration. For example, as shown in FIG. 4, the housing further includes a clip 700 (shown attached to the first housing section), comprising an arm 701, comprising alternatingly opposed teeth 702a and 702b for illustratively, attaching the device to a patient's clothing, bedding, or to another structure attached to the patient (e.g., a plastic loop). In another illustrative alternative, the filter device housing further can further comprise an eyelet, comprising an opening for, illustratively, hanging the filter device to a support during use.

A variety of porous materials are suitable for use as filter elements (including prefilter elements and supports) and vent elements in accordance with embodiments of the invention, and suitable porous materials are known in the art. Preferably, the filter elements and vent elements comprise microporous membranes, and a variety of suitable membranes are known in the art.

Additionally, in those embodiments wherein the filters further comprises supports comprising screens or meshes, a variety of materials are suitable for use as supports, and suitable materials are known in the art.

Hydrophilic membranes suitable for use as filter elements include polymeric membranes. Suitable polymers include, but are not limited to, polyolefins, polyesters, polyamides (for example, any nylon, e.g., Nylon 6, 11, 46, 66, and 610), polyimides, sulfones (e.g., polysulfones, including aromatic polysulfones such as, for example, polyethersulfone, bisphenol A polysulfone, polyarylsulfone, and polyphenylsulfone), polyvinylidene halides (including polyvinylidene fluoride (PVDF)), acrylics, polyacrylonitriles, polyaramides, polyarylene oxides and sulfides, and polymers and copolymers made from halogenated olefins and unsaturated nitriles. Examples include, but are not limited to, polyethylene, polypropylene, polybutylene terephthalate (PBT), polyethylene terephthalate (PET), and Preferred polymers are polysulfones, polyolefins, polyesters, and polyamides.

Other suitable materials include cellulosic derivatives, such as cellulose acetate, cellulose propionate, cellulose acetate-propionate, cellulose acetate-butyrate, and cellulose butyrate. Non-resinous materials, such as glass fibers, may also be used.

Exemplary membranes are disclosed in U.S. Pat. Nos. 4,702,840 and 4,900,449. Other membranes, including those disclosed in U.S. Pat. Nos. 4,906,374; 4,886,836; 4,964,989; 5,019,260; 4,340,479; 4,855,163; 4,744,132; 4,707,266; 4,203,848; 4,618,533, 6,039,872; 6,780,327; 6,783,937; and 7,189,322, may also be suitable.

Fibrous media, for example, non-woven media such as those disclosed in U.S. Pat. No. 5,133,878, may also be suitable.

Particularly preferred are commercially available media, such as those available from Pall Corporation under the trademarks SUPOR®, VERSAPOR®, and POSIDYNE®. Commercially available membranes, such as those available from Pall Corporation under the trademarks ULTIPOR $N_{66}$®, ULTIPOR®, FLUORODYNE®, LOPRODYNE®, CARBOXYDYNE®, IMMUNODYNE®, BIODYNE A®, BIODYNE B®, BIODYNE C®, MUSTANG®, as well as commercially available fibrous media, such as those available from Pall Corporation under the trademark HDC® may also be suitable.

Hydrophobic membranes suitable for use as vent membranes include polymeric membranes. Suitable polymers include, but are not limited to, polyolefins, particularly polypropylene and polymethylpentene; perfluorinated polyolefins, such as polytetrafluoroethylene, polyesters, polyamides, polysulfones, polyacrylonitriles, and polyvinylidene difluoride (PVDF). Suitable membranes include, but are not limited to, those disclosed in International Publication No. WO 91/17809 and U.S. Pat. Nos. 5,126,054 and 5,451,321. In some embodiments, vent membranes can comprise superimposed hydrophobic and hydrophilic membranes, as disclosed in International Publication No. WO 91/17809 and U.S. Pat. Nos. 5,126,054 and 5,451,321. In those embodiments comprising superimposed membranes, the hydrophilic membrane faces liquid, and superimposed membranes allow air or gas to pass through until the hydrophilic membrane is contacted or covered by the liquid.

A filter element and/or a vent membrane can have any suitable pore structure, e.g., a pore size (for example, as evidenced by bubble point, or by $K_L$ as described in, for example, U.S. Pat. No. 4,340,479, or evidenced by capillary condensation flow porometry), a pore rating, a pore diameter (e.g., when characterized using the modified OSU F2 test as described in, for example, U.S. Pat. No. 4,925,572), or removal rating that reduces or allows the passage therethrough of one or more materials of interest as the fluid is passed through the element. The pore structure used depends on the composition of the fluid to be treated, and the desired effluent level of the treated fluid. Filters and vents can comprise multiple layered or composite media.

The pore structure of the filter elements is selected based upon the use of the filter device and the fluid to be filtered as is known in the art. Typically, the filter elements have a pore size of about 5 micrometers or less. In some embodiments wherein the filter is a sterilizing filter, the pore size is, for example, about 0.2 micrometers.

The pore structure, e.g., pore rating, of the vent membrane(s) is preferably selected as is known in the art, e.g., to preclude the passage of the IV fluid therethough at the operating pressures utilized. For example, the pore rating of the vent membrane(s) is typically about 0.3 micrometers or less, more preferably, 0.2 micrometers or less, e.g., in the range of about 0.2 micrometers to about 0.02 micrometers. Vents can comprise multiple layered or composite membranes.

The filter elements and vent membranes can have any desired critical wetting surface tension (CWST, as defined in, for example, U.S. Pat. No. 4,925,572). Typically, the filter elements have a CWST of about 72 dynes/cm (about $72 \times 10^{-5}$ N/cm) or more, in some embodiments, about 80 dynes/cm (about $84 \times 10^{-5}$ N/cm), or more. In some embodiments wherein the filter is a sterilizing filter, the filter elements have CWSTs in the range from about 84 dynes/cm (about $84 \times 10^{-5}$ N/cm) to about 90 dynes/cm (about $90 \times 10^{-5}$ N/cm) or more. Typically, the vent membranes have a CWST in the range of about 22 dynes/cm to about 24 dynes/cm (about $22 \times 10^{-5}$ N/cm to about $24 \times 10^{-5}$ N/cm), though the CWSTs can be higher or lower.

The surface characteristics of the filter element and/or vent membrane and/or the inner surfaces of the housing can be modified (e.g., to affect the CWST, to include a surface charge, e.g., a positive or negative charge, and/or to alter the polarity, hydrophilicity, or hydrophobicity of the surface) by wet or dry oxidation, by coating or depositing a polymer on the surface, or by a grafting reaction. Modifications include, e.g., irradiation, a polar or charged monomer, coating and/or curing the surface with a charged polymer, and carrying out chemical modification to attach functional groups on the surface. Grafting reactions may be activated by exposure to an energy source such as gas plasma, vapor plasma, corona discharge, heat, a Van der Graff generator, ultraviolet light, electron beam, or to various other forms of radiation, or by surface etching or deposition using a plasma treatment.

The total fluid hold up volume of the device may vary depending on, for example, the fluid(s) being filtered, the intended use, and, if the filtered fluid is to be administered, the subject or patient (e.g., a neonatal versus an adult). A typical hold up volume may be in the range of, for example, about 0.1 cc to about 5 cc. In some embodiments, the total hold up volume of the downstream filtrate chambers is about 2 cc or less, preferably, about 1.5 cc or less.

In accordance with an embodiment of the invention, a method for priming a filter device comprises filling the device with liquid, e.g., via gravity or a pump. In those embodiments wherein the device comprises at least one vent, the device preferably self-primes or auto-primes, i.e., the device does not need to be inverted during filling, e.g., if desired, the device can be hung vertically with the inlet positioned upwardly and the outlet positioned downwardly. The upstream inlet chamber can be filled from the bottom up, and air or gas is displaced through the vent membrane(s) and vent port(s) to the outside environment. Filtered fluid fills the downstream filtrate chambers, and, unfiltered fluid continues to displace air or gas through the vent membrane(s) until the upstream inlet chamber is filled with liquid.

Fluids may be processed in accordance with embodiments of the invention for any suitable period of time.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A filter device comprising:
a housing comprising a first section and a second section,
(i) the first section comprising a top wall comprising an outer surface and an inner surface, and at least one side wall, the first section including a first filtrate downstream chamber and a first vent chamber, the first filtrate downstream chamber including a portion of the inner surface of the top wall, and the first vent chamber including another portion of the inner surface of the top wall,
(ii) the second section comprising a bottom wall comprising an outer surface and an inner surface, and at least one side wall, the second section including a second filtrate downstream chamber and a second vent chamber, the second filtrate downstream chamber including a portion of the inner surface of the bottom wall, and the second vent chamber including another portion of the inner surface of the bottom wall;
the housing further comprising an inlet and an outlet, and a cavity bordered by the inner surfaces of the top and bottom walls, and an inner surface of at least one side wall of the first and/or second section;
a filter comprising at least first and second spaced apart porous filter elements, the first and second elements each comprising a hydrophilic membrane, the first and second filter elements each having an upstream surface and a downstream surface, the first filter element being disposed in the housing across a first fluid flow path, and the second filter element being disposed in the housing across a second fluid flow path;

the housing including, in the cavity, an upstream inlet chamber between the upstream surfaces of the first and second filter elements and bordered by the inner surface of at least one side wall of the first and/or second section and the upstream surfaces of the filter elements, the upstream chamber being free of a solid partition between the upstream surfaces of the first and second filter elements;

the housing defining the first fluid flow path between the inlet, the upstream inlet chamber, the first filtrate downstream chamber and the outlet, wherein the first filter element is disposed across the first fluid flow path; and, defining the second fluid flow path between the inlet, the upstream inlet chamber, the second filtrate downstream chamber and the outlet, wherein the second filter element is disposed across the second fluid flow path.

2. A filter device comprising:

a housing comprising a first section and a second section, the first section comprising a top wall comprising an outer surface and an inner surface, the first section including a first filtrate downstream chamber and a first vent chamber, the first filtrate downstream chamber including a portion of the inner surface of the top wall, and the first vent chamber including another portion of the inner surface of the top wall, the second section comprising a bottom wall comprising an outer surface and an inner surface, the second section including a second filtrate downstream chamber and a second vent chamber, the second filtrate downstream chamber including a portion of the inner surface of the bottom wall, and the second vent chamber including another portion of the inner surface of the bottom wall;

the housing further comprising an inlet and an outlet, opposing first side walls and opposing second side walls, wherein the first and/or second housing sections comprise opposing first side walls having inner surfaces, and the first and/or second housing sections comprise opposing second side walls having inner surfaces, and the housing comprises a cavity bordered by the inner surfaces of the top, bottom, and side walls;

a filter comprising at least first and second spaced apart porous filter elements, each filter element comprising a hydrophilic membrane, the first and second filter elements each having an upstream surface and a downstream surface, the first filter element being disposed in the housing across a first fluid flow path, and the second filter element being disposed in the housing across a second fluid flow path;

the housing including, in the cavity, an upstream inlet chamber between the upstream surfaces of the first and second filter elements and bordered by the inner surfaces of the side walls and the upstream surfaces of the filter elements, the upstream chamber being free of a solid partition between the upstream surfaces of the first and second filter elements;

the housing defining the first fluid flow path between the inlet, the upstream inlet chamber, the first filtrate downstream chamber and the outlet, wherein the first filter element is disposed across the first fluid flow path; and, defining the second fluid flow path between the inlet, the upstream inlet chamber, the second filtrate downstream chamber and the outlet, wherein the second filter element is disposed across the second fluid flow path.

3. A filter device comprising:

a housing comprising a first section and a second section, (i) the first section comprising a top wall comprising an outer surface and an inner surface, and at least one side wall, the first section including a first filtrate downstream chamber, the first filtrate downstream chamber including a portion of the inner surface of the top wall, (ii) the second section comprising a bottom wall comprising an outer surface and an inner surface, and at least one side wall, the second section including a second filtrate downstream chamber, the second filtrate downstream chamber including a portion of the inner surface of the bottom wall;

the housing further comprising an inlet and an outlet, and a cavity bordered by the inner surfaces of the top and bottom walls, and an inner surface of at least one side wall of the first and/or second section;

a filter comprising at least first and second spaced apart porous filter elements, each filter element comprising a hydrophilic membrane, the first and second filter elements each having an upstream surface and a downstream surface, the first filter element being disposed in the housing across a first fluid flow path, and the second filter element being disposed in the housing across a second fluid flow path;

the housing including, in the cavity, an upstream inlet chamber between the upstream surfaces of the first and second filter element and bordered by the inner surface of at least one side wall of the first and/or second section and the upstream surfaces of the filter elements;

the housing defining the first fluid flow path between the inlet, the upstream inlet chamber, the first filtrate downstream chamber and the outlet, wherein the first filter element is disposed across the first fluid flow path; and, defining the second fluid flow path between the inlet, the upstream inlet chamber, the second filtrate downstream chamber and the outlet, wherein the second filter element is disposed across the second fluid flow path;

wherein the top wall inner surface of the first filtrate downstream chamber and the bottom wall inner surface of the second filtrate downstream chamber each comprise a plurality of ridges providing a plurality of channels, the channels directing fluid from the downstream surfaces of the first and second filter elements to the housing outlet and wherein the top wall inner surface of the first filtrate downstream chamber and the bottom wall inner surface of the second filtrate downstream chamber each comprise a central channel that is wider and/or deeper than the other channels, and, wherein each central channel has side, top, and bottom walls forming a closed tube for at least a majority of the length of each central channel.

4. The filter device of claim 1, wherein the first vent chamber further comprises a first vent port and a first vent including a first microporous vent element arranged to allow gas to pass through the first vent element and the first vent port; and wherein the second vent chamber further comprises a second vent port and a second vent including a second microporous vent element arranged to allow gas to pass through the second vent element and the second vent port.

5. The filter device of claim 1, wherein at least a portion of the top wall of the first filtrate downstream chamber and at least a portion of the bottom wall of the second filtrate downstream chamber is transparent or translucent.

6. The filter device of claim 1, wherein the top wall inner surface of the first filtrate downstream chamber and the bottom wall inner surface of the second filtrate downstream chamber each comprise a plurality of ridges providing a plurality of channels, the channels directing fluid from the downstream surfaces of the first and second filter elements to the housing outlet.

7. The filter device of claim 6, wherein the top wall inner surface of the first filtrate downstream chamber and the bottom wall inner surface of the second filtrate downstream chamber each comprise a central channel that is wider and/or deeper than the other channels.

8. The filter device of claim 7, wherein each central channel has side, top, and bottom walls forming a closed tube for at least a majority of the length of each channel.

9. The filter device of claim 7, wherein the ridges providing each central channel are sealed to the downstream surface of the filter element.

10. A method of filtering a fluid, comprising passing the fluid through the filter device of claim 1.

* * * * *